United States Patent
Kojima et al.

(10) Patent No.: US 8,951,521 B2
(45) Date of Patent: Feb. 10, 2015

(54) COMPOUNDS HAVING ACTIVITY OF SUPPRESSING ACTIVATION OF TGF-β RECEPTOR, METHOD FOR SCREENING OF THE COMPOUNDS, AND COMPOSITION FOR PREVENTING OR TREATING DISEASE CAUSED BY HEPATITIS C VIRUS

(75) Inventors: Soichi Kojima, Wako (JP); Mitsuko Hara, Wako (JP); Takehisa Matsumoto, Yokohama (JP); Daisuke Takaya, Yokohama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 13/819,979

(22) PCT Filed: Aug. 30, 2011

(86) PCT No.: PCT/JP2011/069620
§ 371 (c)(1),
(2), (4) Date: Jun. 4, 2013

(87) PCT Pub. No.: WO2012/029792
PCT Pub. Date: Mar. 8, 2012

(65) Prior Publication Data
US 2013/0244253 A1  Sep. 19, 2013

(30) Foreign Application Priority Data
Aug. 30, 2010  (JP) ................................ 2010-192803

(51) Int. Cl.
| | | |
|---|---|---|
| A61K 39/00 | (2006.01) | |
| A61K 39/395 | (2006.01) | |
| C12N 9/99 | (2006.01) | |
| C07K 16/28 | (2006.01) | |
| C07K 16/40 | (2006.01) | |
| C12Q 1/37 | (2006.01) | |

(52) U.S. Cl.
CPC .............. *C12N 9/99* (2013.01); *C07K 16/2863* (2013.01); *C07K 16/40* (2013.01); *C12Q 1/37* (2013.01); *C07K 2317/76* (2013.01); *G01N 2500/02* (2013.01); *C07K 2317/34* (2013.01)
USPC .................. 424/139.1; 424/158.1; 424/130.1

(58) Field of Classification Search
None
See application file for complete search history.

(56) References Cited

U.S. PATENT DOCUMENTS

| | | | |
|---|---|---|---|
| 2006/0286105 A1 | 12/2006 | Ledbetter et al. | |
| 2009/0004182 A1 | 1/2009 | Baiocchi et al. | |
| 2011/0091994 A1* | 4/2011 | Lotteau | 436/501 |

FOREIGN PATENT DOCUMENTS

| | | | |
|---|---|---|---|
| JP | 11-124398 A | 5/1999 | |
| JP | 11-127861 A | 5/1999 | |
| JP | 2001-103993 A | 4/2001 | |
| JP | 2006-525362 A | 11/2006 | |
| JP | 2008-515983 A | 5/2008 | |
| WO | 2008013928 | 1/2008 | |
| WO | WO 2008/013928 | * 1/2008 | ............. A61K 48/00 |

OTHER PUBLICATIONS

Verga-Gerard et al. Mar. 2011. Journal of Hepatology, (Mar. 2011) vol. 54, No. Suppl. 1, pp. S324. Meeting Info.: 46th Annual Meeting of the European-Association-for-the-Study-of-the-Liver (EASL. Berlin, Germany.*
De Chassey et al. 2008. Mo Syst. Biol. 4:230.*
Takamasa Ueno et al.,"Isolation and Characterization of Monoclonal Antibodies That Inhibit Hepatitis C Virus NS3 Protease", Journal of Virology, Jul. 2000, pp. 6300-6308, vol. 74, No. 14.
Soichi Kojima et al., HCV NS3 Protease Mimics TGF-β2 and Activities TGF-β Signals Via Type I Receptor, Hepatology,Oct. 2011, p. 1327A, 2060 , vol. 54, No. 4 (Suppl).
Petra Franzen et al., Cloning of a TGFβ Type I Receptor that forms a Heteromeric Complex with the TGFβ Type II Receptor, Cell, 1993, vol. 75, No. 19, pp. 681-692.
Scott L. Friedman, "Mechanism of Hepatic Fibrogenesis", Gastroenterology, 2008, pp. 1655-1669, vol. 134 No. 6.
Scott L. Friedman, "Hepatic Stellate Cells: Protean, Multifunctional, and Enigmatic Cells of the Liver", Physiol. Rev., Jan. 2008, pp. 125-172, vol. 88, No. 1.
Joan Massague, "TGFβ in Cancer", Cell, Jul. 2008, pp. 215-230, vol. 134, No. 2.
Nature Reviews Drug Discovery,"Protease inhibitors show promise against HCV" Jan. 2009, p. 11, vol. 8, No. 1.
Alisa Opar Nature Reviews Drug Discovery, "Excitement Grows for Potential Revolution in Hepatitis C virus Treatment" Jul. 2010, pp. 501-503, vol. 9, No. 7.
International Search Report of PCT/JP2011/069620 dated Nov. 22, 2011.

* cited by examiner

*Primary Examiner* — Shulamith H Shafer
(74) *Attorney, Agent, or Firm* — Sughrue Mion, PLLC

(57) ABSTRACT

An object is to provide a compound capable of inhibiting activation of TGF-β receptors due to HCV, and a screening method for the compound. It has been found that a HCV-derived NS3 protease binds to type I TGF-β receptor, and this binding results in activation of TGF-β receptors. Moreover, binding sites between the NS3 protease and type I TGF-β receptor were identified, and it has been found that antibodies recognizing these binding sites inhibit activation of TGF-β receptors due to NS3 protease. Furthermore, it has been also found that screening for a compound capable of inhibiting activation of TGF-β receptors can be performed by using the inhibition of the binding between NS3 protease and type I TGF-β receptor or the like as an index.

3 Claims, 14 Drawing Sheets

Fig. 5

```
APITAYSQQTRGLLGCIITSL
TGRDKNQVEGEVQVVSTAIQS
FLATCVNGCWTVYHGAGSKTLAGPKGPIAQMY
TNVDQDLVGWPAPPGARSLIP
CTCGSSDLYLVTRHADVIPVRR
RGDNRGSLLSPRPVSYLKGSS
GGPLLCPSGHAVGVFRAAVCTRGVAKAVDFVPVESMETTMRS
```
(Seq ID No:8)

Fig. 6

```
ALQCFCHLCTKDNFTCVTDGLC
EVSVIETTDKVIHNSM
C
IAEIDLIPRDRPEV
CAPSSKIGSVITTY
CCNQDHCNKIEL
```
(Seq ID No:9)

Fig. 11

[Figure: Bar graph showing TGF-β activity (relative value) on y-axis (0 to 4) with NS3 (100μg/ml) treatment. Conditions from top to bottom: CONTROL; Antibodies to Type I receptor — Binding Site2-Rabbit 1 at 10, 5, 2.5, 1.25; Binding Site3-Rabbit 1 at 10, 5, 2.5, 1.25; Non-immunized mouse antibody at 10, 5, 2.5, 1.25.]

Fig. 13

COMPOUNDS HAVING ACTIVITY OF SUPPRESSING ACTIVATION OF TGF-β RECEPTOR, METHOD FOR SCREENING OF THE COMPOUNDS, AND COMPOSITION FOR PREVENTING OR TREATING DISEASE CAUSED BY HEPATITIS C VIRUS

TECHNICAL FIELD

The present invention relates to a compound having an activity of inhibiting activation of TGF-β receptors, and a screening method for the compound. More specifically, the present invention relates to a compound having an activity of inhibiting binding between NS3 protease and type I TGF-β receptor, and thereby inhibiting activation of TGF-β receptors due to the NS3 protease, and a screening method for the compound.

BACKGROUND ART

Hepatic cirrhosis is the ninth most common cause of death in Japan ("Summary of Monthly Report of Vital Statistics: 2009," Ministry of Health, Labour and Welfare), and there are approximately 300,000 patients and approximately 3,500,000 potential hepatitis patients in Japan. This disease is an intractable disease in which hardening of the liver tissue occurs due to abnormal accumulation of extracellular matrix proteins. This disease includes a series of pathological conditions where the hardening of the liver (fibrosis of the liver) occurs during repetitions of hepatic impairment and regeneration, and apoptosis of the liver cells consequently occurs, leading to liver failure.

A known major causative factor of the liver fibrosis is activation of the fibrogenic cytokine TGF-β (NPL 1). In hepatic cirrhosis, hepatic stellate cells present between the hepatic sinusoid and hepatic parenchymal cells are activated and start to excessively produce extracellular matrices including collagen. The excessive collagen production and the like are promoted by TGF-β. It has been shown in an animal model that hepatic cirrhosis can be prevented when the action of TGF-β is blocked by a gene therapy or the like (NPL 2). Moreover, hepatic cancer develops from cirrhotic liver at an incidence of 5 to 7 percent per year, leading to death. It is said that TGF-β also plays an important role as a causative factor of the hepatic cancer through induction of EMT (epithelial-mesenchymal transition) and reduction in immunity to cancer due to induction of regulatory T cells (NPL 3).

On the other hand, 76% of the hepatic cirrhosis cases in Japan are caused by hepatitis C virus (HCV) infection. In Japan alone, two million people are estimated to be infected with HCV, and it is said that 200 million people are infected with HCV in the world. Hepatic cirrhosis develops 10 years to 30 years after infection with HCV, and further progresses to hepatic cancer. Hence, this becomes a great social problem. Under such circumstances, a combination therapy of PEGylated interferon with ribavirin is applied at present, and a virus removal effect is observed in 40 to 50% of patients. Moreover, protease activity inhibitors against serine protease NS3 necessary for maturation of virus particles have been developed, and are currently in Phase II to III clinical trials (NPLs 4 to 5).

However, as the mechanism by which HCV causes liver fibrosis and/or hepatic cancer has not been elucidated, no drug has yet been developed which enables a radical treatment for such viral diseases.

CITATION LIST

Non Patent Literature

[NPL 1] Friedman S L, Gastroenterol, May 2008, 134 (6), pp. 1655-69
[NPL 2] Friedman S L, Physiol Rev., January 2008, Vol. 88, No. 1, pp. 125-172
[NPL 3] Massague J, Cell, July 2008, Vol. 134, No. 2, pp. 215-230
[NPL 4] Nature Reviews Drug Discovery, January 2009, Vol. 8, No. 1, pp. 11
[NPL 5] Nature Reviews Drug Discovery, July 2010, Vol. 9, No. 7, pp. 501-503

SUMMARY OF INVENTION

Technical Problem

The present invention has been made in view of the problem of the conventional technologies, and an object of the present invention is to provide a compound capable of inhibiting activation of TGF-β receptors due to HCV, a screening method for the compound, and a composition for preventing or treating a disease caused by hepatitis C virus.

Solution to Problem

The present inventors have conducted earnest study to achieve the above object. As a result, the present inventors have found that HCV-derived NS3 protease binds to type I TGF-β receptor, and the binding results in activation of TGF-β receptors. In addition, it is also found that the activation results in an enhancement of collagen production in hepatic stellate cells and liver cells, which causes fibrosis of the liver. Furthermore, binding sites between NS3 protease and type I TGF-β receptor were identified, and it was found that antibodies which recognize these binding sites inhibit the activation of TGF-β receptors due to NS3 protease. These findings have led to the completion of the present invention.

More specifically, the present invention provides the following inventions.
(1) A compound having an activity of inhibiting binding between NS3 protease and type I TGF-β receptor, and thereby inhibiting activation of TGF-β receptors due to the NS3 protease.
(2) The compound according to (1), which has an activity of binding to any one of the NS3 protease and the type I TCF-β receptor.
(3) The compound according to (2), which has an activity of binding to a peptide comprising an amino acid sequence shown in any one of SEQ ID NOs: 1 to 6.
(4) The compound according to any one of (1) to (3), which is an antibody to any one of the NS3 protease and the type I TGF-β receptor.
(5) A composition for preventing or treating a disease caused by hepatitis C virus, comprising the compound according to any one of (1) to (4) as an active ingredient.
(6) A screening method for a compound having an activity of inhibiting activation of TGF-β receptors due to NS3 protease, the method comprising the following steps (a) to (c):
(a) a step of bringing NS3 protease and type I TGF-β receptor in contact with each other in the presence of a test compound;
(b) a step of detecting binding between the NS3 protease and the type I TGF-β receptor; and (c) a step of selecting the compound if the compound inhibits the binding.

(7) A screening method for a compound having an activity of inhibiting activation of TGF-β receptors due to NS3 protease, the method comprising the following steps (a) to (c):

(a) a step of bringing NS3 protease and type I TGF-β receptor in contact with each other in the presence of a test compound;

(b) a step of detecting activation of TGF-β receptors due to the NS3 protease; and (c) a step of selecting the compound if the compound inhibits the activation.

(8) A method for inhibiting activation of TGF-β receptors due to NS3 protease, the method comprising inhibiting binding between the NS3 protease and type I TGF-β receptor.

(9) A method for preventing or treating a disease caused by hepatitis C virus, the method comprising inhibiting binding between NS3 protease and type I TGF-β receptor.

Advantageous Effects of Invention

The present invention makes it possible to provide a compound capable of inhibiting activation of TGF-β receptors due to HCV, a screening method for the compound, and, in turn, a composition for preventing or treating a disease caused by hepatitis C virus.

BRIEF DESCRIPTION OF DRAWINGS

FIG. 5 is a drawing of amino acid sequences (SEQ ID NO: 8) showing putative binding sites and putative contact residues of the NS3 protease bound to the type I TGF-β receptor.

FIG. 6 is a drawing of amino acid sequences (SEQ ID NO: 9) showing putative binding sites and putative contact residues of the type I TGF-β receptor bound to the NS3 protease.

FIG. 11 is a graph showing that the anti-type I TGF-β receptor antibodies inhibit TGF-β signal activation due to NS3 protease in a dependent manner on the dose of the antibodies, under a condition that each anti-type I TGF-β receptor antibody and ×9CAGA/CCL64 cells are preincubated.

FIG. 13 is a graph showing that anti-NS3 antibodies do not inhibit TGF-β signal activation due to TGF-β2, under a condition that each anti-NS3 antibody and TGF-β2 are preincubated.

DESCRIPTION OF EMBODIMENTS

Figure 1:
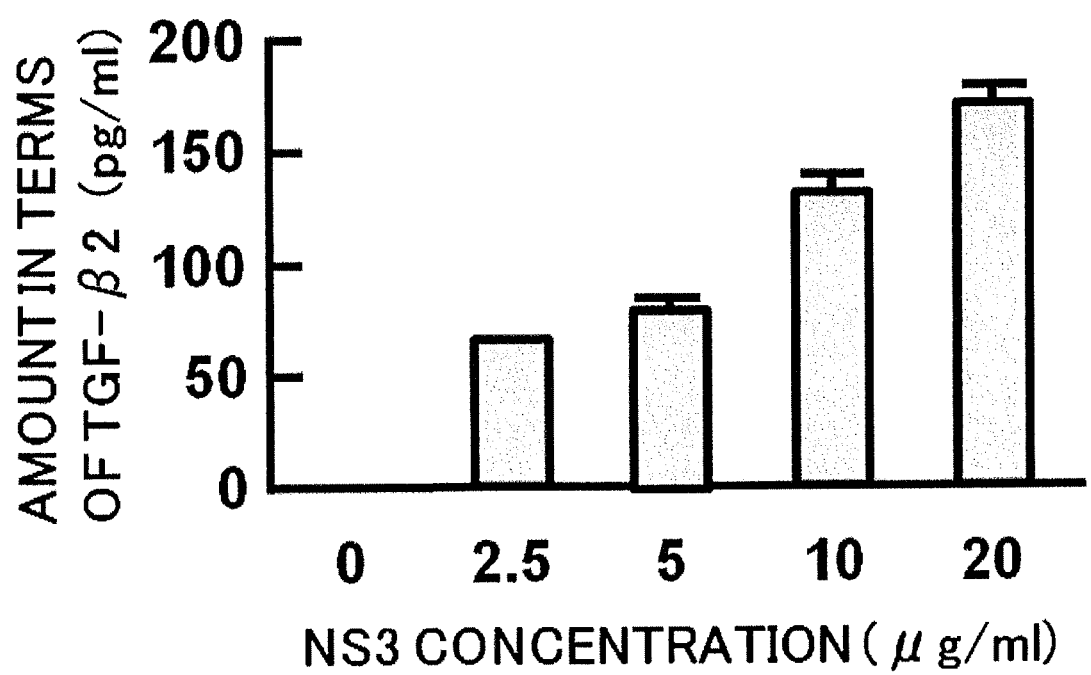
FIG. 1 is a graph showing that NS3 protease has a TGF-β2-like antigenic activity.

A compound of the present invention is characterized by having an activity of inhibiting binding between NS3 protease and type I TGF-β receptor, and thereby inhibiting activation of TGF-β receptors due to the NS3 protease.

The NS3 protease is a nonstructural protein from hepatitis C virus (HCV), and is composed of 631 amino acids. The NS3 protease comprises a protease domain at the N-terminal and a helicase domain at the C-terminal. Typical examples of the protease domain and the helicase domain are a peptide comprising 1056th to 1204th amino acids and a peptide comprising 1224th to 1455th amino acids in the protein identified by GenBank™ ACCESSION No. AAB27127.1, respectively.

Meanwhile, the type I TGF-β receptor forms a complex with type II TGF-β receptor through binding to TGF-β, which is a ligand of these receptors. A typical human-derived example of the type I TGF-β receptor is a protein identified by GenBank ACCESSION No. BAG63449.1.

Moreover, the activation of TGF-β receptors in the present invention means that the TGF-β receptors form the complex to assume a state of enabling downstream signal transduction. This signal transduction may cause, for example, the following: phosphorylation of the type I TGF-β receptor occurring after the formation of the complex; phosphorylation of Smad2/3 by the phosphorylated type I TGF-β receptor; formation of a complex of the phosphorylated Smad2/3 with Smad4; translocation of the Smad complex into a nucleus; and transcriptional activation of a target gene by the Smad complex translocated into the nucleus.

Note that the "inhibition" in the present invention includes both complete inhibition (prevention) and partial inhibition.

In addition, the compound of the present invention is not particularly limited, as long as the substance is capable of inhibiting binding between NS3 protease and type I TGF-β receptor, and thereby inhibiting activation of TGF-β receptors due to the NS3 protease. From the viewpoint of inhibiting the binding, the compound of the present invention is preferably one having an activity of binding to NS3 protease or type I TGF-β receptor, and more preferably one having an activity of binding to the amino acid sequence shown in anyone of the following SEQ ID NOs: 1 to 6, i.e., a peptide comprising a binding site between NS3 protease and type I TGF-β receptor. Moreover, from the viewpoint of specifically inhibiting the binding between NS3 protease and type I TGF-β receptor without affecting activation due to TGF-β2, the compound of the present invention is particularly preferably one having an activity of binding to a peptide comprising the amino acid sequence shown in the following SEQ ID NOs: 1 to 3.

TGRDKNQVEGEVQVVSTATQS (SEQ ID NO: 1)

TNVDQDLVGWPAPPGARSLTP (SEQ ID NO: 2)

RGDNRGSLLSPRPVSYLKGSS (SEQ ID NO: 3)

FVSVTETTDKVIHNSM (SEQ ID NO: 4)

IAEIDLIPRDRPFV (SEQ ID NO: 5)

CAPSSKTGSVTTTY. (SEQ ID NO: 6)

Note that the amino acid sequences shown in SEQ ID NOs: 1 to 3 represent binding sites on the NS3 protease side, and the amino acid sequences shown in SEQ ID NOs: 4 to 6 represent binding sites on the type I TGF-β receptor side.

One form of the compound of the present invention is an antibody. The "antibody" in the present invention encompasses all classes and all subclasses of immunoglobulin. The meaning of "antibody" encompasses polyclonal antibodies and monoclonal antibodies, as well as the forms of functional fragments of antibodies.

In addition, the antibody of the present invention encompasses chimeric antibodies, humanized antibodies, human antibodies, and functional fragments of these antibodies. Examples of the functional fragments of antibodies include Fab, Fab', F(ab')2, a variable region fragment (Fv), a disulfide-stabilized Fv, a single-chain Fv (scFv), sc(Fv)2, a diabody, a polyspecific antibody, polymers thereof, and the like.

When the antibody of the present invention is administered to a human as a drug, the antibody is desirably a chimeric antibody, a humanized antibody, or a human antibody from the viewpoint of reducing adverse effects.

Regarding the antibody, a polyclonal antibody can be obtained by immunizing a host animal with an antigen (the inflammatory cytokine or the like), and purifying the polyclonal antibody from an antiserum of the animal in a conventional manner (for example, salting-out, centrifugation, dialysis, column chromatography, or the like). Meanwhile, a monoclonal antibody can be prepared by a hybridoma method, a recombinant DNA method, or the like.

A chimeric antibody can be obtained, for example, as follows. Specifically, a mouse is immunized with an antigen. An antibody variable domain (variable region) which binds to the antigen is cut from the gene encoding a monoclonal antibody of the mouse. The antibody variable domain is linked with a gene encoding a human bone marrow-derived antibody constant domain (constant region). These linked genes are incorporated into an expression vector. The expression vector is then introduced into a host, and causes the host to produce a chimeric antibody. (For example, Japanese Patent Application Publication No. Hei 7-194384, Japanese Patent No. 3238049, U.S. Pat. No. 4,816,397, U.S. Pat. No. 4,816,567, and U.S. Pat. No. 5,807,715).

A humanized antibody can be prepared by, for example, grafting a gene sequence of an antigen binding site (CDR) of a non-human-derived antibody to a human antibody gene (CDR grafting) (see, for example, Japanese Patent No. 2912618, Japanese Patent No. 2828340, Japanese Patent No. 3068507, European Patent No. 239400, European Patent No. 125023, International Publication No. WO 90/07861, and International Publication No. WO 96/02576).

A human antibody can be prepared by, for example, using a transgenic animal (for example, a mouse) capable of producing a repertoire of human antibodies (for example, Nature, 362: 255-258 (1992), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese Patent Application Publication No. Hei 10-146194, Japanese Patent Application Publication No. Hei 10-155492, Japanese Patent No. 2938569, Japanese Patent Application Publication No. Hei 11-206387, International Application Japanese-Phase Publication No. Hei 8-509612, and International Application Japanese-Phase Publication No. Hei 11-505107).

The antibody used in the present invention encompasses antibodies whose amino acid sequences are modified, without reduction in the desired activity (the activity of inhibiting binding between NS3 protease and type I TGF-β receptor, and thereby inhibiting activation of TGF-β receptors due to the NS3 protease). Note that whether or not such a desired activity is reduced in a modified antibody can be checked by using an assay system for activity described in a screening method to be described later.

An amino acid sequence variant of the antibody of the present invention can be prepared by introducing a mutation into a DNA encoding an antibody chain of the present invention, or by peptide synthesis. Examples of such a modification include substitution, deletion, addition and/or insertion of residues in the amino acid sequence of the antibody of the present invention. The position where the amino acid sequence of the antibody is modified may be in a constant region of a heavy chain or a light chain of the antibody, or in a variable region (a framework region or a CDR) thereof, as long as the antibody has an activity at the same level as that of the unmodified antibody. It is conceivable that an amino acid modification in a region other than CDR has a relatively small influence on the binding affinity for an antigen. Currently, an approach is known in which amino acids in CDR are modified, and screening is conducted for an antibody with an enhanced affinity for an antigen (PNAS, 102: 8466-8471 (2005), Protein Engineering, Design & Selection, 21: 485-493 (2008), International Publication No. WO 2002/051870, J. Biol. Chem., 280: 24880-24887 (2005), and Protein Engineering, and Design & Selection, 21: 345-351 (2008)).

In addition, the modification of the antibody may be, for example, a modification of a posttranslational process of the antibody, such as change in number, positions, or kinds of glycosylated moieties. Typically, glycosylation of an antibody is N-linked glycosylation or O-linked glycosylation. The glycosylation of an antibody depends greatly on a host cell used to express the antibody. The modification of a glycosylation pattern can be performed by a known method such as introduction or deletion of a specific enzyme involved in sugar production (Japanese Patent Application Publication No. 2008-113663, Japanese Patent No. 4368530, Japanese Patent No. 4290423, U.S. Pat. No. 5,047,335, U.S. Pat. No. 5,510,261, U.S. Pat. No. 5,278,299, and International Publication No. WO99/54342). Moreover, in the present invention, an amino acid susceptible to deamidation or an amino acid adjacent to an amino acid susceptible to deamidation may be substituted with a different amino acid to prevent the deamidation for the purposes of increasing the stability of the antibody and the like. Moreover, the stability of the antibody can also be increased by substituting a glutamic acid with a different amino acid. The antibody used in the present invention also provides an antibody stabilized in such a manner.

The antibody used in the present invention only needs to have an activity of inhibiting binding between NS3 protease and type I TGF-β receptor, and thereby inhibiting activation of TGF-β receptors due to the NS3 protease, as described above. However, the antibody is preferably an antibody to NS3 protease or type I TGF-β receptor. From the viewpoint of specifically inhibiting the binding between NS3 protease and type I TGF-β receptor, antibodies which binds to peptides comprising the amino acid sequences shown in SEQ ID NOs: 1 to 6 are more preferable. Furthermore, of these antibodies, antibodies which bind to peptides comprising the amino acid sequences shown in SEQ ID NOs: 1 to 3 are particularly preferable, from the viewpoint of specifically inhibiting the binding between NS3 protease and type I TGF-β receptor, without affecting activation due to TGF-β2.

In addition, another form of the compound of the present invention is a polypeptide having a dominant negative phenotype over NS3 protease, type I TGF-β receptor, or the like in the binding between NS3 protease and type I TGF-β receptor and the activation of TGF-β receptors due to the NS3 protease. Examples of such a polypeptide include polypeptides obtained by way of substitution, deletion, addition and/or insertion in the amino acid sequence shown in any one of SEQ ID NOs: 1 to 6, and polypeptides selected from a peptide library by a screening method to be described later. Such a dominant negative polypeptide can be produced by a recombinant DNA method, chemical synthesis, or the like.

Moreover, another form of the compound of the present invention is a low molecular weight compound which has an activity of inhibiting activation of TGF-β receptors due to NS3 protease, and which is capable of inhibiting the binding between NS3 protease and type I TGF-β receptor. Such a low molecular weight compound can be obtained by, for example, designing and synthesizing a low molecular weight compound based on the structure of a peptide moiety comprising the amino acid sequence shown in any one of SEQ ID NOs: 1 to 6 in NS3 protease or type I TGF-β receptor, or selecting a low molecular weight compound from a library of synthetic low molecular weight compounds by the screening method to be described later.

In addition, the present invention provides a composition comprising the compound of the present invention. The form of the composition of the present invention may be a pharmaceutical composition, a food or beverage (including an animal feed), or a reagent used for research purpose (for example, for an in vitro or in vivo experiment).

Since the composition of the present invention comprises the compound of the present invention as an active ingredient, the composition has an activity of inhibiting binding between NS3 protease and type I TGF-β receptor, and thereby inhibiting activation of TGF-β receptors due to the NS3 protease. Therefore, the composition of the present invention can be used preferably as a pharmaceutical composition to be administered for preventing or treating a disease caused by hepatitis C virus, i.e., acute hepatitis, chronic hepatitis, hepatic cirrhosis, hepatic cancer, or the like.

Since the composition of the present invention comprises the compound of the present invention, the composition can also be used preferably as a food or beverage to be ingested daily for preventing or ameliorating these diseases.

Moreover, since the composition of the present invention comprises the compound of the present invention, the composition of the present invention can be used preferably as a reagent for inhibiting binding between NS3 protease and type I TGF-β receptor, and thereby inhibiting activation of TGF-β receptors due to the NS3 protease.

A pharmaceutical preparation can be prepared from the composition of the present invention by a known pharmaceutical method. For example, the composition of the present invention can be used orally or parenterally in the forms of capsules, tablets, pills, liquids, powders, granules, fine granules, film coated preparations, pellets, troches, sublingual preparations, chewables preparations, buccal preparations, pastes, syrups, suspensions, elixirs, emulsions, liniments, ointments, plasters, cataplasms, transdermal preparations, lotions, inhalants, aerosols, injections, suppositories, and the like.

For preparing these pharmaceutical preparations, the composition of the present invention can be combined, as appropriate, with carriers which are pharmacologically acceptable or acceptable in a food and/or a beverage. Specific examples of the carriers include sterilized water, physiological saline, vegetable oils, solvents, base agents, emulsifiers, suspending agents, surfactants, stabilizers, flavoring agents, aromatics, excipients, vehicles, antiseptics, binders, diluents, tonicity adjusting agents, soothing agents, bulking agents, disintegrators, buffering agents, coating agents, lubricants, coloring agents, sweeteners, thickening agents, flavor modifiers, solubilizers, and other additives, and the like.

When the composition of the present invention is used as a pharmaceutical composition, the composition may be used in combination with a known pharmaceutical composition used for preventing or treating a disease caused by hepatitis C virus. Examples of the known drug include PEG interferon and ribavirin. Furthermore, it is also conceivable to use the composition of the present invention in combination with any of NS3 protease activity inhibitors (Telaprevir by Vertex, Boceprevir by Schering-Ploug, and the like) which are currently in Phase III clinical trials. These activity inhibitors are the same as the compound of the present invention in that these are directed to NS3 protease. However, the target of the activity inhibitors is activity of the protease necessary for maturation of HCV viral particles, and these activity inhibitors are different from the compound of the present invention in terms of point of action in the pathogenic mechanism of a disease caused by hepatitis C virus. Hence, it can be expected that the use of the compound of the present invention in combination with PEG interferon, ribavirin, and an NS3 protease activity inhibitor makes it possible to stop the progression of the pathological condition caused by hepatitis C virus, eliminate the virus, and achieve a radical treatment for a liver disease caused by hepatitis C virus, with reduced concentrations of the drugs used.

When the composition of the present invention is used as a food or beverage, the food or beverage may be, for example, a health food, a functional food, a food for specified health use, a dietary supplement, a food for patients, a food additive, or an animal feed. In addition to ingestion in the forms of the above-described compositions, the food or beverage of the present invention can be ingested in the forms of various foods and beverages. Specific examples of the foods and beverages include products containing oils, such as edible oils, dressings, mayonnaises, and margarines; liquid foods such as soups, dairy beverages, refreshing beverages, tea beverages, alcoholic beverages, drink preparations, jelly beverages, and functional beverages; carbohydrate-containing foods such as rice food products, noodles, and breads; processed animal foods such as hams and sausages; processed fishery foods such as steamed fish paste (Kamaboko), dried fishes, and salted fish guts (Shiokara); processed vegetable foods such as pickles; semi solid foods such as jellies and yogurt; fermented foods such as fermented soybean pastes and fermented beverages; various confectionery products such as Western confectionery products, Japanese confectionery products, candies, chewing gums, gummies, cold desserts, and frozen desserts; retort pouch products such as curries, thick starchy sauces, and Chinese soups; instant foods such as instant soups and instant soy-bean soups; microwavable foods; and the like. Moreover, the examples of the foods and beverages also include health foods and beverages prepared in the forms of powders, granules, tablets, capsules, liquids, pastes, or jellies. The composition of the present invention can be used for amimals including human. The animals other than human are not particularly limited, and the composition of the present invention can be used for various kinds of livestock, poultry, pets, experimental animals, and the like. Specific examples of the animals include pig, cattle, horse, sheep, goat, chicken, wild duck, ostrich, domesticated duck, dog, cat, rabbit, hamster, mouse, rat, monkey, and the like, but are not limited thereto.

The production of the food or beverage of the present invention can be carried out based on a production technology known in the technical field. One or more components effective for preventing or ameliorating a disease caused by hepatitis C virus may be added to the food or beverage. Moreover, a multifunctional food or beverage may be produced by combination with another component or another functional food which exhibits a function other than the prevention or amelioration of a disease caused by hepatitis C virus.

When the composition of the present invention is administered or ingested, the amount of the composition administered or ingested is selected, as appropriate, according to the age, body weight, symptom, health conditions of a subject, the kind of the composition (a drug, a food, a beverage, or the like) and the like. For example, the amount of the composition of the present invention per single administration or ingestion is generally 0.01 mg/kg body weight to 100 mg/kg body weight.

A product (a drug, a food or beverage, or a reagent) of the composition of the present invention and a manual thereof may be provided with an indication stating that the product is used for inhibiting activation of TGF-β receptors due to NS3 protease. Here, "a product or a manual provided with an indication" means that an indication is provided to a main body, a container, or a package of the product, or an indication is provided to a manual, a package insert, an advertisement, other printed matters, or the like in which information of the product is disclosed. The indication stating that the product is used for inhibiting activation of TGF-β receptors due to NS3 protease can include information about the mechanism of the inhibition of the activation of TGF-β receptors due to NS3 protease brought about by the administration or ingestion of the composition of the present invention. Regarding the mechanism, for example, information regarding the inhibition of binding between NS3 protease and type I TGF-β receptor, and the resultant inhibition of the activation of TGF-β receptors due to the NS3 protease may be included. In addition, the indication stating that the product can be used for inhibiting the binding between NS3 protease and type I TGF-β receptor can include information regarding use of the product for prevention, treatment, or the like of a disease caused by hepatitis C virus.

Moreover, in the present invention, the administration of the compound or the composition of the present invention to a subject, the ingestion thereof by a subject, or the like makes it possible to inhibit binding between NS3 protease and type I TGF-β receptor, and thereby inhibit activation of TGF-β receptors due to the NS3 protease, as mentioned above. Moreover, the inhibition of the activation also makes it possible to prevent or treat a disease caused by hepatitis C virus. Hence, the present invention also provides a method for inhibiting activation of TGF-β receptors due to NS3 protease, the method being characterized by inhibition of binding between the NS3 protease and type I TGF-β receptor, as well as a method for preventing or treating a disease caused by hepatitis C virus, the method being characterized by inhibition of binding between NS3 protease and type I TGF-β receptor.

Moreover, the present invention provides a screening method for a compound having an activity of inhibiting activation of TGF-β receptors due to NS3 protease, the method comprising the following steps (a) to (c):

(a) a step of bringing NS3 protease and type I TGF-β, receptor in contact with each other in the presence of a test compound;

(b) a step of detecting binding between the NS3 protease and the type I TGF-β receptor; and (c) a step of selecting the compound if the compound inhibits the binding.

The test compound used in the screening method of the present invention is not particularly limited, and examples thereof include expression products of gene libraries, libraries of synthetic low molecular weight compounds, peptide libraries, antibodies, substances released from bacteria, extraction liquids or culture supernatants of cells (microorganisms, plant cells, or animal cells), purified or partially purified polypeptides, extracts of a marine organism, plant, or animal origin, soil, and random phage peptide display libraries. Note that the compound selected by the screening method has the activity of inhibiting binding between NS3 protease and type I TGF-β receptor, and thereby inhibiting activation of TGF-β receptors due to the NS3 protease. Hence, such a compound can be a candidate for an agent for preventing or treating a disease caused by hepatitis C virus, as described above.

In addition, the NS3 protease and the type I TGF-β receptor used here are as follows. For example, the NS3 protease may be a peptide comprising 1056th to 1204th amino acids and 1224th to 1455th amino acids in the protein identified by GenBank ACCESSION No. AAB27127.1, whereas the type I TGF-β receptor may be the protein identified by GenBank ACCESSION No. BAG63449.1. Fragments, altered proteins, modified proteins, and the like retaining activities of binding to the corresponding ones can be used, in addition to such naturally occurring proteins. For example, it is possible to use a protein obtained by expression as a fusion protein with a marker protein for easy detection, an enzyme such as alkaline phosphatase (SEAP) or β-galactosidase, or a fluorescent protein such as glutathione S-transferase (GST) or green fluorescent protein (GFP). The type I TGF-β receptor may be used in the form of being expressed on a cell surface. In addition, regarding the NS3 protease, NS3 protease fused with a partial sequence of NS4A on the N-terminal side of the NS3 protease can also be used as described in Examples, which will be described later. Note that NS4A is a protein from HCV, as in the case of the NS3 protease. NS4 Å is a protein which binds to the N-terminal portion of NS3 protease to form a complex, and functions as a cofactor to enhance the protease activity.

In the step (a), NS3 protease and type I TGF-β receptor, which are capable of binding to each other, are brought into contact with each other in the presence of a test compound. The contact only needs to be conducted under conditions where the binding between the NS3 protease and the type I TGF-β receptor is not inhibited, if the test compound is absent.

Moreover, in the step (b), the binding between the NS3 protease and the type I TGF-β receptor is detected. For detecting the binding, a known approach can be employed, as appropriate, without any particular limitation. For example, it is possible to employ immunoprecipitation, yeast two-hybrid system, an ELISA method, a method using a detector (for example, BIAcore (manufactured by GE Healthcare)) based on the surface plasmon resonance phenomenon, or a method based on FRET (fluorescence resonance energy transfer).

Furthermore, in the step (c), the compound is selected, if the compound inhibits the binding. For example, when immunoprecipitation is used, the evaluation can be conducted by comparing the amount of the type I TGF-β receptor coprecipitated when the NS3 protease is precipitated by an antibody specific thereto in the presence of a test compound with the amount (control value) of the type I TGF-β receptor coprecipitated in the absence of the test compound. Specifically, when the amount of the type I TGF-β receptor in the presence of the test compound is smaller than the amount in the absence of the test compound (for example, when the value is 80% or less, 50% or less, or 30% or less of the control value), the test compound is evaluated as a compound having an activity of inhibiting activation of TGF-β receptors due to NS3 protease. When a method other than the immunoprecipitation is used for the detection of the binding, evaluation can be conducted in a similar manner by using the degree of the binding in the absence of the test compound as a control value.

Moreover, the present invention also provides a screening method for a compound having an activity of inhibiting activation of TGF-β receptors due to NS3 protease, the method comprising the following steps (a) to (c):

(a) a step of bringing NS3 protease and type I TGF-β receptor in contact with each other in the presence of a test compound;

(b) a step of detecting activation of TGF-β receptors due to the NS3 protease; and (c) a step of selecting the compound if the compound inhibits the binding.

The test compound, NS3 protease, type I TGF-β receptor, and step (a) used in this screening method are the same as those of the above-described screening method.

In addition, in the step (b), the activation of TGF-β receptors due to NS3 protease is detected. A known approach can be employed, as appropriate, for the detection of the activation, without any limitation. For example, it is possible to employ detection of phosphorylation of the type I TGF-β receptor, Smad2/3, or the like using a phosphorylated site-specific antibody, detection of translocation of a Smad complex labeled with a fluorescent protein or the like into the nucleus, or reporter assay described in Examples 6 to 8, which will be described later.

Furthermore, in the step (c), the compound is selected if the compound inhibits the activation. For example, when reporter assay is used, the evaluation can be conducted by comparing a value of luciferase activity in the presence of the test compound with a value (control value) of luciferase activity in the absence of the test compound. Specifically, when the value of luciferase activity in the presence of the test compound is smaller than the value in the absence of the test compound (for example, when the value is 80% or less, 50% or less, or 30% or less of the control value), the test compound can be evaluated as a compound having an activity of inhibiting activation of TGF-β receptors due to NS3 protease. When a method other than the reporter assay is used for the detection of the activation, evaluation can be conducted in a similar manner by using the degree of the activation in the absence of the test compound as a control value.

Hereinafter, the present invention will be described more specifically based on Examples and Comparative Examples. However, the present invention is not limited to Examples below. Note that a "purified recombinant NS3 protein" used in Examples was prepared as follows.

<Purified Recombinant NS3 Protein>

First, *Escherichia coli* strain KRx was cultured which was transformed with a plasmid vector pET32a(+) (manufactured by Novagen) into which a gene encoding scNS4A-NS3 protease (see Protein Sci., 1998, Vol. 7, No. 10, pp. 2143 to 2149, a protein comprising the amino acid sequence shown in SEQ ID NO: 7) was inserted. Here, the scNS4A-NS3 protease was a protein in which a partial sequence (1678th to 1690th amino acids, GSVVIVGRIILSG (residues 1-13 of SEQ ID NO: 7), in the protein identified by GenBank ACCESSION No. AAB27127.1) of NS4A from HCV was fused, through a linker (SGS), to a NS3 protease domain region (1027th to 1445th amino acids in the protein identified by GenBank ACCESSION No. AAB27127.1) from HCV at the N-terminal thereof (1027th to 1206th amino acids in the protein). Then, the expression of the target protein to which a trx-His-S tag from a pET32a (+) vector was added was induced by IPTG (isopropyl-β-thiogalactopyranoside). After that, the bacterial cells were collected. The collected bacterial cells were suspended in a buffer (20 mM Tris-HCl [pH 8.0], 300 mM NaCl, 4 mM $MgCl_2$, 10% glycerol, 1 mM DTT, and 0.1% n octyl-β-o-glucopyranoside), and then disrupted by sonication followed by centrifugation. The separated supernatant was filtered through a filter having a pore size of 0.45 μm. The filtered supernatant was subjected to affinity purification using a HisTrap HP column (manufactured by GE Healthcare), then subjected to buffer exchange with another buffer (20 mM Tris-HCl [pH 8.0], 300 mM NaCl, 0.1 mM $CaCl_2$, and 2 mM DTT) by using a HiPrep 26/60 Desalting column (manufactured by GE Healthcare), and then passed through a EndoTrap Blue column (manufactured by GE Healthcare) to remove LPS. Then, the collected flow-through was used as a purified recombinant NS3 protein in Examples.

Example 1

Confirmation of TGF-β2-like Antigenic Activity of NS3 Protease

First, to investigate the presence or absence of the relationship between the HCV-derived NS3 protease and the TGF-β signal transduction, the TGF-β2-like antigenic activity of the purified recombinant NS3 protein was studied by an ELISA method using TGF-β2 Emax (R) ImmunoAssay System (manufactured by Promega). Specifically, the TGF-β coat antibody included in the kit was diluted 1:1000 with a carbonate buffer solution (pH 9.2), added to a 96-well ELISA plate (manufactured by NUNC) at 100 μl/well, and allowed to stand at 4° C. overnight to coat the plate. The coated plate was washed with a phosphate buffer containing 0.05% Tween 20 (hereinafter, this buffer is also referred to as "PBST"). Then, the TGF-β blocking solution included in the kit was added at 270 μl/well, and allowed to stand at 37° C. for 35 minutes to perform blocking. Next, the plate subjected to the blocking treatment was washed with PBST, and a prepared TGF-β2 standard solution and the purified recombinant NS3 protein solution were added to the plate, which was then allowed to stand at 4° C. overnight. Note that the purified recombinant NS3 protein was diluted with the TGF-β sample diluting solution included in the kit at final concentrations of 2.5, 5, 10, and 20 μg/ml, and each of the diluted protein solutions was added at 100 μl/well as an ELISA sample. The plate to which the samples were added was washed with PBST, and then an anti-TGF-β2 polyclonal antibody diluted 1:2000 with the TGF-β sample diluting solution was added at 100 μl/well, followed by shaking at room temperature for 2 hours. Then, the plate to which the polyclonal antibody was added was washed with PEST, and peroxidase-labeled TGF-β diluted 1:100 with the TGF-β sample diluting solution was added at 100 μl/well. Then, the plate was allowed to stand at room temperature for 2 hours. The plate to which the TGF-β was added was washed with PBST, and then a TMB (tetramethyl benzidine) solution was added at 100 μl/well as a chromogenic substrate for a peroxidase substrate. Color development was conducted at room temperature for 15 minutes at the maximum. At the time when sufficient color development was obtained, the reaction was stopped by adding an equivalent amount of 1 mol/l hydrochloric acid. After that, the absorbance of each well in the plate was measured at a wavelength of 450 nm. Then, a standard curve was prepared by using TGF-β2 Standard. The TGF-β2-like antigenic activity of the purified recombinant NS3 protein was found in terms of amount of active TGF-β2. FIG. 1 shows the obtained results.

As is apparent from the results shown in FIG. 1, it was confirmed that the HCV-derived NS3 protease exhibited a TGF-β2-like antigenic activity, and it has been suggested that the NS3 protease is involved in the TGF-β signal transduction in liver cells at the time of HCV infection. In addition, the antigenic activity of the NS3 protease was about 1/50000 to 1/100000 as strong as that of TGF-β2.

Example 2

Examination of TGF-β Signal activation due to NS3 protease

Figure 2:
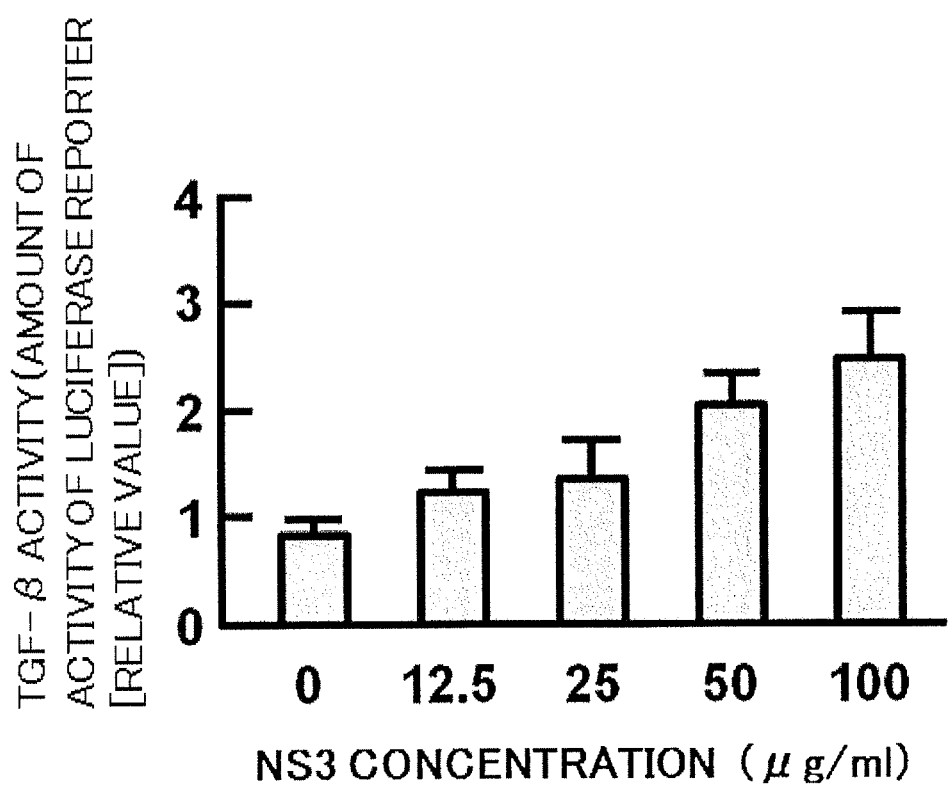
FIG. 2 is a graph showing that the NS3 protease activates TGF-β signal.

Next, whether or not the HCV-derived NS3 protease was capable of activating TGF-β signal in cells was investigated by reporter assay. Specifically, the TGF-β2-like activity of the purified recombinant NS3 protein was investigated by using a cell line (hereinafter, also referred to as "×9CAGA/CCL64 cells") established by introducing, into mink lung epithelial cells (CCL64 cell), a pGL reporter plasmid (manufactured by Promega) into which 9 DNA binding sequences (CAGA) of a transcription factor Smad important for transcription of a TGF-(3-target gene were inserted upstream of a luciferase gene. Specifically, the ×9CAGA/CCL64 cells were suspended at 2×10$^5$ cells/ml in a Dulbecco's modified Eagle's medium (DMEM, manufactured by Invitrogen) supplemented with 10% fetal bovine serum (manufactured by EQUITECH-BIO) and an 1% antiseptic (a penicillin-streptomycin-glutamine solution, manufactured by Invitrogen) (hereinafter, this medium is also referred to as "culture medium"). The suspension was seeded in a 96-well cell culture plate (manufactured by TPP) at 100 μl/well, and the cells were cultured overnight at 37° C. in the presence of 5% $CO_2$. Then, the culture supernatant was removed by suction from the plate, and the cells were washed with a calcium-magnesium-containing phosphate buffer (hereinafter, also referred to as "PBS(+)"). Then, 100 μl of DMEMs which contained 0.1% bovine serum albumin (manufactured by EQUITECH-BIO) and the 1% antiseptic (hereinafter, such a DMEM is also referred to as a "treatment medium") and which were supplemented with the purified recombinant NS3 protein at final concentrations of 12.5, 25, 50, and 100 μg/ml, respectively, were added to the cells, and the cells were cultured at 37° C. in the presence of 5% $CO_2$ for additional 20 hours. The next day, the luciferase activity in the cells in the plate was measured by using a luciferase assay system (manufactured by Promega) according to the package insert of the kit. Specifically, the culture supernatant was removed by suction, and the cells were washed with PBS(+). Then, 20 μl of a liquid obtained by diluting Passive Lysis Buffer (5×) included in the kit 1:1 was added to each well, and the cells were lysed by shaking at room temperature for 15 minutes. In the meantime, one vial of Luciferase Assay Substrate was dissolved in 10 ml of Luciferase Assay Reagent II (hereinafter, also referred to as "LARII solution"), and the solution was then dispensed in advance into a 96-well luciferase assay plate (manufactured by Costar) at 100 μl/well. Next, 10 μl of each cell lysate was added to the LARII solution dispensed in advance, and mixed therewith by pipetting, followed by measurement for the emission intensity with a luminometer (product name: ARVO™, manufactured by PerkinElmer). The sample size was 3 for each treatment. With the reporter activity of untreated cells being regarded as 1, amounts of activity of the cells treated with the purified recombinant NS3 protein were determined in the form of relative values. FIG. 2 shows the obtained results.

As is apparent from the results shown in FIG. 2, the purified recombinant NS3 protein increased the luciferase activity in a concentration dependent manner. This suggests that the NS3 protease acts on TGF-β receptor in some manner, and activates the TGF-β signal.

Example 3

Figure 3:
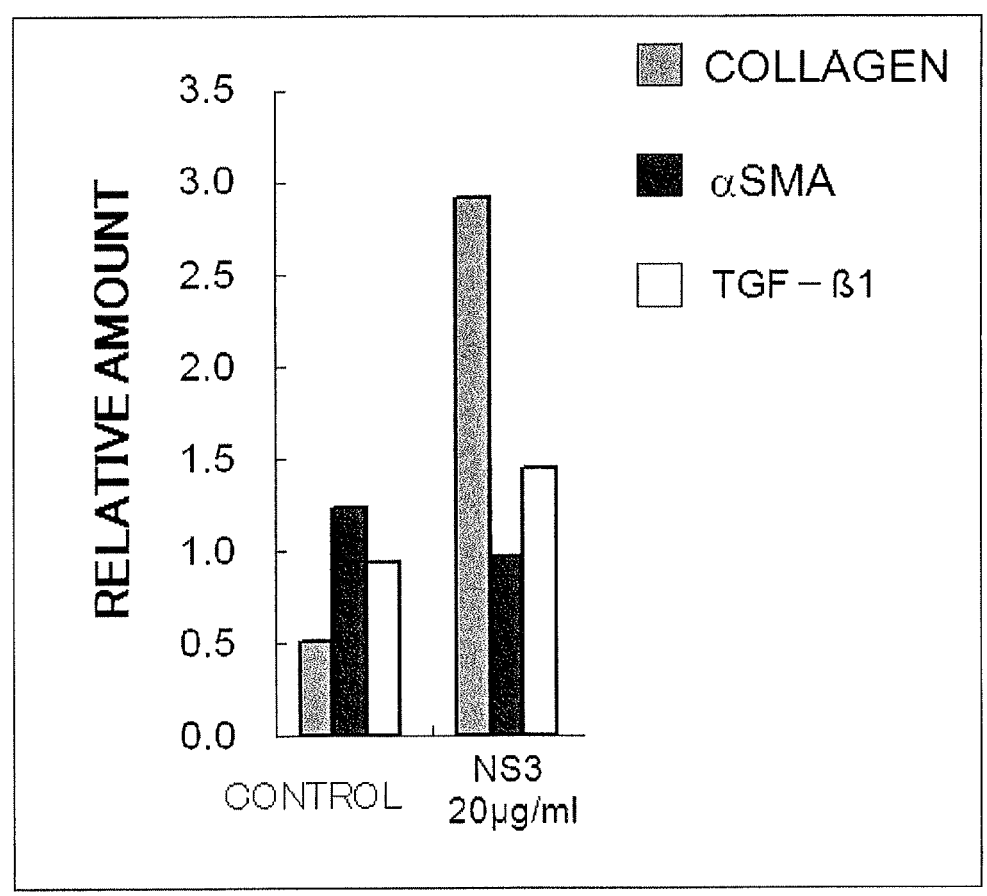
FIG. 3 is a graph showing that the NS3 protease promotes collagen production.

Examination of Enhancement of Collagen Production in Hepatic Stellate Cells by NS3 Protease TGF-β is known to act on liver stellate cells, promotes abnormal production of collagen from stellate cells, and thereby causes fibrosis of the liver. In this respect, the relationship between the NS3 protease and an enhancement in the collagen production was next investigated. Specifically, the abdomen of a Wistar rat (kept under SPF, male, 15 weeks old) was opened under pentobarbital anesthesia, and then a catheter was inserted into the portal vein. Perfusion was performed with a washing liquid for blood removal, with a 0.06% Pronase solution (manufactured by Carbiochem), and with a 0.03% collagenase (manufactured by Wako Pure Chemical Industries, Ltd.) solution, in this order. After that, the liver was isolated, and incubated in a solution obtained by adding 1 ml of 2 mg/ml DNaseI (manufactured by Roche Diagnostics) to a hepatic stellate cell isolation buffer solution containing 0.057% Pronase and 0.057% collagenase, for 30 minutes in a hot bath of 36° C. Note that, during the incubation, the pH of the lysate was kept between 7.2 to 7.4 with 1 N NaOH. Next, the liver tissue lysate was filtered through a mesh, and the total volume was adjusted to 150 ml by adding the hepatic stellate cell isolation buffer solution, and the lysate was dispensed into three 50-ml polypropylene tubes, followed by centrifugation at 4° C. and 2000 rpm for 8 minutes. Moreover, the supernatant in each polypropylene tube was removed by suction, and 0.2 ml of a DNaseI solution was added to each tube. A Gey's balanced salt solution was added to each tube, and the liquids were mixed with each other by pipetting. The total volume was adjusted to 100 ml, and the liquid was again dispensed into two 50-ml polypropylene tubes, followed by centrifugation at 4° C. and 2000 rpm for 8 minutes. The supernatant in each polypropylene tube was removed by suction, and then 0.2 ml of DNaseI solution was added to each tube. The Gey's balanced salt solution was added to tube, and the liquids were mixed with each other by pipetting. Then, with the total volume being adjusted to 67.5 ml, the liquid was transferred to a beaker, and 27 ml of a Nycodenz (manufactured by SIGMA) solution sterilized through a 0.22-μm filter (a final concentration of 7.75%) was added to the beaker, followed by mixing. The cell solution was dispensed into eight 15-ml tubes, and 1 ml of the Gey's balanced salt solution was layered thereon, followed by centrifugation at 4° C. and 3200 rpm for 15 minutes. Thus, hepatic stellate cells were isolated. The isolated hepatic stellate cells were suspended at a concentration of $1\times10^5$ cells/ml in a OMEN medium containing 10% fetal bovine serum (manufactured by EQUITECH-BIO) and a 1% antiseptic (manufactured by Invitrogen), seeded in cell culture dishes (manufactured by CORNING) having a diameter of 6 cm at 3 ml/dish, and cultured overnight at 37° C. in the presence of 5% $CO_2$. The next day, the medium was exchanged, and simultaneously a treatment was started with the purified recombinant NS3 protein at a final concentration of 20 μg/ml. The cells were cultured for 7 days, while the medium was exchanged every other day. In addition, as a control, cells (untreated cells) not treated with the purified recombinant NS3 protein or the like were also prepared, and cultured for 7 days, while the medium was exchanged every other day. Seven days later, mRNAs were extracted from these cells by using an RNA purification kit, RNeasy Micro Kit (manufactured by QIAGEN), and the concentration of the mRNAs was determined by measuring the absorbance at 260 nm with a spectrophotometer (Nano Drop). Subsequently, a RT reaction was carried out by using the mRNAs as templates and using PrimeScript™ RT reagent Kit (manufactured by TAKARA) according to the package insert. Moreover, a reaction liquid was prepared by using SYBR® Premix EX Taq™ II (manufactured by TAKARA) according to the package insert, and PCR reactions were carried out by using primers (manufactured by Invitrogen) for collagen (Collagen(I) α1), a smooth muscle actin (αSMA), TGF-β1, and an internal standard, GAPDH. The amounts of mRNA expression were compared with those of the untreated cells. FIG. 3 shows the obtained results.

As is apparent from the results shown in FIG. 3, it was found that the expression of the Collagen(I) α1 gene in the cultured rat primary hepatic stellate cells treated with the purified recombinant NS3 protein was increased by approximately 6 times, as compared with that of the untreated cells, indicating that the NS3 protease remarkably promoted the collagen production in hepatic stellate cells.

Note that it has already been known that activation of TGF-β does not change the amount of expression of the αSMA gene, which is a marker of activation of the stellate cells, or the amount of expression of the TGF-β1 gene. As is apparent from the results shown in FIG. 3, it was shown that the treatment on the stellate cells with the NS3 protease did not change the amounts of expression of these genes.

Therefore, from the results shown in Examples 1 to 3, it has been suggested that the NS3 protease acts by presumably binding to the TGF-β receptors as in the case of TGF-β, activates the TGF-β receptors to transmit the TGF-β signal, and promotes the collagen production, so that the liver fibrosis is caused.

Example 4

Docking-Simulation between NS3 Protease and Type I TGF-β Receptor

It is known that TGF-β forms a complex with type I TGF-β receptor and type II TGF-β receptor for signal transduction (see "Joan Massague, Mol Cell, Feb. 1, 2008, Vo. 29, No. 2, pp. 149-150"). Hence, the TGF-β-like activity of NS3 protease suggests molecular-biologically that the complex of NS3 protease and type I TGF-β receptor is formed by intermolecular interaction acting therebetween. In this respect, a protein-protein docking-simulation was conducted to investigate the presence or absence of protein-protein interaction therebetween. In addition, which amino acid residues in the NS3 protease and the TGF-β receptor are involved in such an interaction was predicted.

Note that although no complete protein-protein interaction prediction apparatus has existed as of now, a method in which learning from an existing protein-protein interaction database is utilized, a method based on empirical physical functions, and the like have been proposed. The method carried out here was a method in which the degrees of geometric complementarity between proteins (in other words, recesses and protrusions of the proteins) were exhaustively evaluated, and was implemented based on the description in "Molecular surface recognition: Determination of geometric fit between proteins and their ligands by correlation techniques", Proc. Natl. Acad. Sci., March 1993, Vol. 89, pp. 2195-2199." Specifically, coordinates of proteins were projected onto three-dimensional grids separated from each other at regular intervals. A surface score and an intramolecular score were assigned to each grid. This operation was conducted on the receptor and the ligand. Then, convolution between the obtained grids was performed, surfaces were explored exhaustively, and the complementarities of binding states were calculated based on the scores. In short, evaluation was made based on the assumption that the higher the score (the complementarity score), the better the complementarity. Note that an advantage of this method is as follows. Specifically, since the scores can be calculated by converting the protein coordinates to three-dimensional grid coordinates, and by applying a fast Fourier transform thereto, the execution speed is high. Hence, the complementarity between the ligand surface and the entire receptor surface can be taken into consideration, instead of the complementarity between the ligand surface and part of the receptor. Moreover, another advantage of this method is that binding sites can be predicted, even when no binding sites are designated from the outside.

Figure 4:
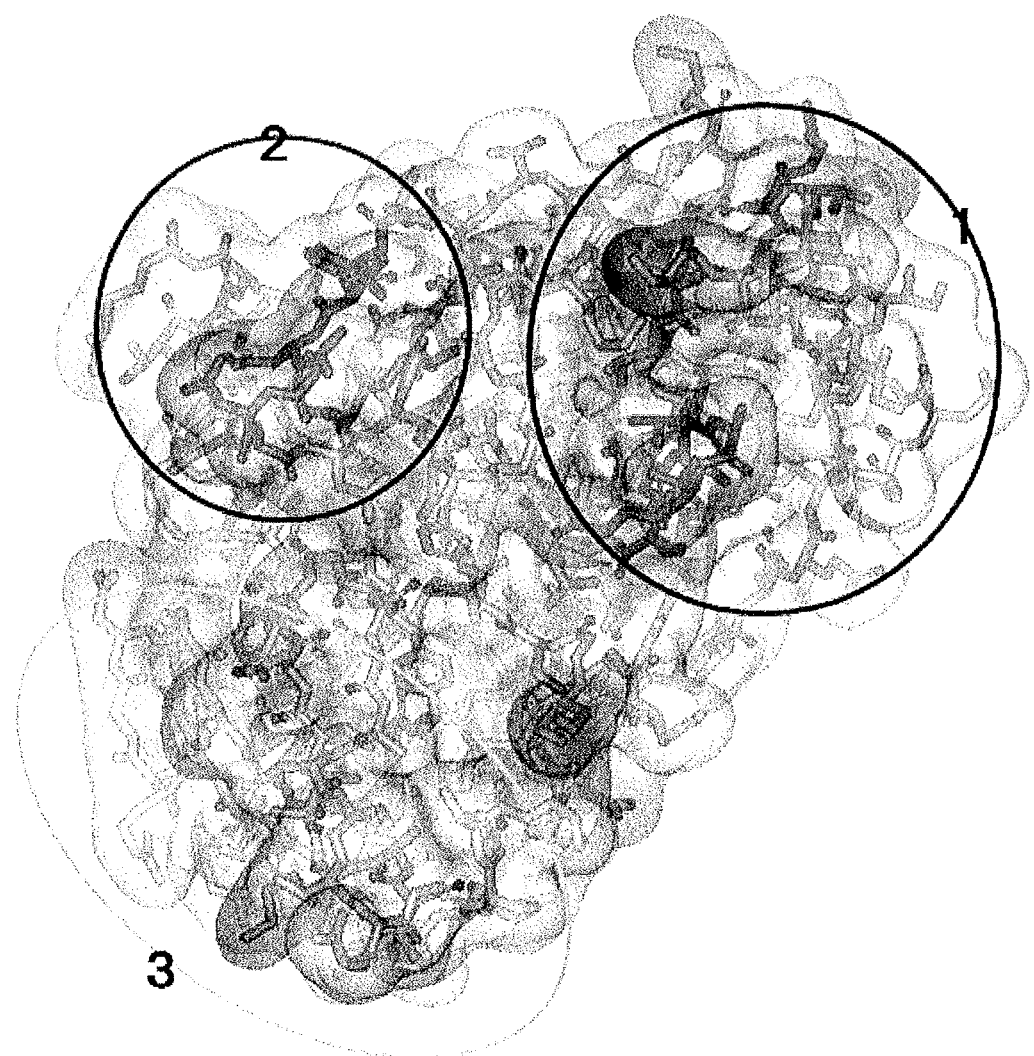
FIG. 4 is a diagram showing putative binding sites of the NS3 protease bound to type I TGF-β receptor.

Specifically, HCV NS3 protease PDB code: 1NS3, and chain B (type-II) and chain C (type-I) of type I TGF-β, receptor PDB code 2PJY were employed for the coordinates of proteins in this example. FIG. 4 shows the obtained results. Note that 360×360×180/12=18000 structures were generated as candidate structures by combining Euler angles of every 12.0 degrees. The putative structure shown in FIG. 4 represents 20 structures with 20 highest complementarity scores. The distribution of the scores of the 20 structures was as follows: 760, 740, 731, 720, 708, 690, 687, 686, 684, 684, 682, 677, 669, 666, 663, 662, 662, 661, 660, and 659. The average value was 435.5, the median was 428.0, and the standard deviation was 54.6.

In addition, amino ac id residues appearing frequently in binding states with high complementarity scores can be estimated to be residues which are highly likely to appear in the interaction with an actual receptor. Hence, amino acid residues with an interatomic distance of 3.8 Å or less in the putative binding states are defined as contact residues, and regarded as putative contact residues of NS3 protease and type I TGF-β receptor. FIGS. 5 and 6 show the obtained results. Note that the amino acid sequences shown in FIG. 5 represent amino acid sequences (amino acid sequences shown in SEQ ID NO: 8) in the protease domain of the NS3 protease, whereas the amino acid sequences shown in FIG. 6 represent amino acid sequences (amino acid sequences shown in SEQ ID NO: 9) in the extracellular domain of the type I TCF-β receptor. In addition, in FIGS. 5 and 6, the underlined amino acid residues represent amino acid residues (putative contact residues) with interatomic distances of 3.8 Å or less in the putative binding state, and the shaded sites represent sites (putative binding sites) involved in the binding between the NS3 protease and the type I TGF-β receptor.

As a result of employment of the above-described approach, it has been predicted that the NS3 protease and the type I TGF-β receptor bind to each other at three sites, as is apparent from the results shown in FIG. 4. In addition, as shown in FIGS. 5 and 6, sites (putative binding sites) and amino acid residues (putative contact residues) involved in such binding were also estimated.

Example 5

Method for Preparing Antibodies

In order to demonstrate that the NS3 protease and the type I TGF-β receptor bind to each other through the putative binding sites (the amino acid sequences shown in SEQ ID NOs: 1 to 6), so that the activation of TGF-β receptors due to NS3 protease is caused, synthetic peptides and the like were prepared based on the amino acid sequences in the putative binding sites, and polyclonal antibodies were produced whose antigens are such synthetic peptides or the like in the following manner.

<Preparation of Synthetic Peptides>

Table 1 shows a list of sequences of synthetic peptides used for preparing polyclonal antibodies targeted to the putative binding sites (the amino acid sequences shown in SEQ ID NOs: 1 to 6) in the NS3 protease or the type I TGF-β receptor. Note that "NH2" and "COOH" in Table 1 represent the N-terminal side and the C-terminal side of each synthetic peptide, respectively. Moreover, "C" on the N-terminal side represents a cysteine residue necessary for binding mcKLH, which will be described later, to each synthetic peptide. Furthermore, "miniPEG" represents a polyethylene glycol having an average molecular weight of 6,000 which was inserted as a spacer molecule, and which was provided for improving the steric hindrance between the antigenic peptide and a carrier-protein.

deprotection and cleavage from the resin with a cleavage cocktail containing 95% TFA. The synthesized peptides were purified by HPLC. Then, mcKLH (manufactured by PIERCE) was bound as a carrier protein to each of the obtained synthetic peptides to provide an antigenicity.

<Preparation of Antiserum to Purified Recombinant NS3 Protein>

Two rabbits (female, Japanese white species (healthy)) were immunized with the purified recombinant NS3 protein. Specifically, for the initial immunization, 150 μg per rabbit of the purified recombinant NS3 protein in Freund's complete adjuvant was intradermally administered, and for the following immunizations, 300 μg of the purified recombinant NS3 protein in the adjuvant was intradermally administered, or 50 μg of the purified recombinant NS3 protein in phosphate buffered saline (PBS) was administered to the auricular vein. The immunization was performed every two weeks in the case of using the Freund's complete adjuvant, or every week in the case of using the PBS. Then, seven days after the final immunization, the whole blood was collected from the heart. The collected blood was allowed to stand overnight at 4° C., and then the serum components were isolated by centrifugation for use as an antiserum. To the obtained antiserum, sodium azide was added at a concentration of 0.1%, and the antiserum was stored at 4° C. In addition, the antibody titer in the serum was determined by an ELISA method. In this assay, a microtiter plate was first coated with a recombinant protein diluted with PBS. Subsequently, the serum, serially diluted, was added to wells washed and blocked with 0.2% Tween 20/PBS, and was incubated. Antibodies to the immunogen were detected by a peroxidase-conjugated antibody to rabbit immunoglobulin.

<Preparation of Antisera to Synthetic Peptides>

For each of the synthetic peptides bound to KLH, two rabbits (female, Japanese white rabbit (healthy)) were immunized with the synthetic peptide by intradermal administration. Specifically, in the first immunization, 300 ug per rabbit of the KLH-conjugated synthetic peptide in Freund's complete adjuvant was administered, and in the following immunizations, 300 ug of the KLH-conjugated synthetic peptide in the adjuvant was administered. The immunization was con-

TABLE 1

| Synthetic peptide | Sequence |
| --- | --- |
| Putative binding site 1 on NS3 protease side (NS-1) | NH2-C-TGRDKNQVEGEVQVVSTATQS-COOH (SEQ ID NO: 10) |
| Putative binding site 2 on NS3 protease side (NS-2) | NH2-C-TNVDQDLVGWPAPPGARSLTP-COOH (SEQ ID NO: 11) |
| Putative binding site 3 on NS3 protease side (NS-3) | NH2-C-RGDNRGSLLSPRPVSYLKGSS-COOH (SEQ ID NO: 12) |
| Putative binding site 1 on type 1 TGF-β receptor side (FB1R1) | NH2-C-miniPEG-FVSVTETTDKVIHNSM-COOH (SEQ ID NO:13) |
| Putative binding site 2 on type 1 TGF-β receptor side (FB1R2) | NH2-C-miniPEG-IAEIDLIPRDRPFV-COOH (SEQ ID NO: 14) |
| Putative binding site 3 on type 1 TGF-β receptor side (FB1R3) | NH2-CAPSSKTGSVTTTY-COOH (SEQ ID NO: 6) |

The peptides shown in Table 1 were synthesized by the Fmoc solid-phase synthesis method (BIO MATRIX RESEARCH, INC.). The final peptides were prepared by ducted every two weeks. Seven days after the final immunization, the whole blood was collected from the heart. The collected blood was allowed to stand overnight at 4° C., and then the serum components were isolated by centrifugation for use as an antiserum. To the obtained antiserum, sodium azide was added at a concentration of 0.1%, and the antiserum was stored at 4° C. The antibody titer in the serum was determined by an ELISA method. In this assay, a microtiter plate was first coated with the synthetic peptide diluted with PBS. Subsequently, the serum, serially diluted, was added to wells washed and blocked with 0.2% Tween 20/PBS, and was incubated. Antibodies to the synthetic peptide were detected by a peroxidase-conjugated antibody to rabbit immunoglobulin.

<Purification of Polyclonal Antibodies from Antisera>

The antiserum to the purified recombinant NS3 protein prepared as described above was diluted with an equal amount of a binding buffer, and then filtered through a filter to remove insoluble matters. In a usual, manner, the filtrate was passed through and adsorbed onto a column packed with ProteinA-sepharose4B (manufactured by GE Healthcare), so that the antibody components were adsorbed onto the column. Non-specifically adsorbed components were removed. Then, components released under an acidic condition were collected. Thus, a purified polyclonal antibody was obtained. The obtained purified antibody was dialyzed against 100 volumes of a PBS buffer solution for exchange, and then sodium azide was added thereto at a final concentration of 0.1%.

Meanwhile, the antisera to the synthetic peptides prepared as described above were subjected to affinity purification by using antigen columns for the antisera, respectively. Specifically, each of the synthetic peptides was bound to CNBr-activated Sepharose 4B (manufactured by GE Healthcare) in a usual manner to obtain the antigen column. The antiserum diluted with an equal amount of a binding buffer was filtered through a filter to remove insoluble matters. Then, the filtrate was passed through the antigen column, so that specific antibodies were adsorbed onto the antigen column. Non-specifically adsorbed components were removed. Then, components released under an acidic condition were collected. Thus, a purified polyclonal antibody was obtained. The obtained purified antibody was dialyzed against 100 volumes of a PBS buffer solution for exchange, and then sodium azide was added thereto at a final concentration of 0.1%.

Example 6

Figure 7:
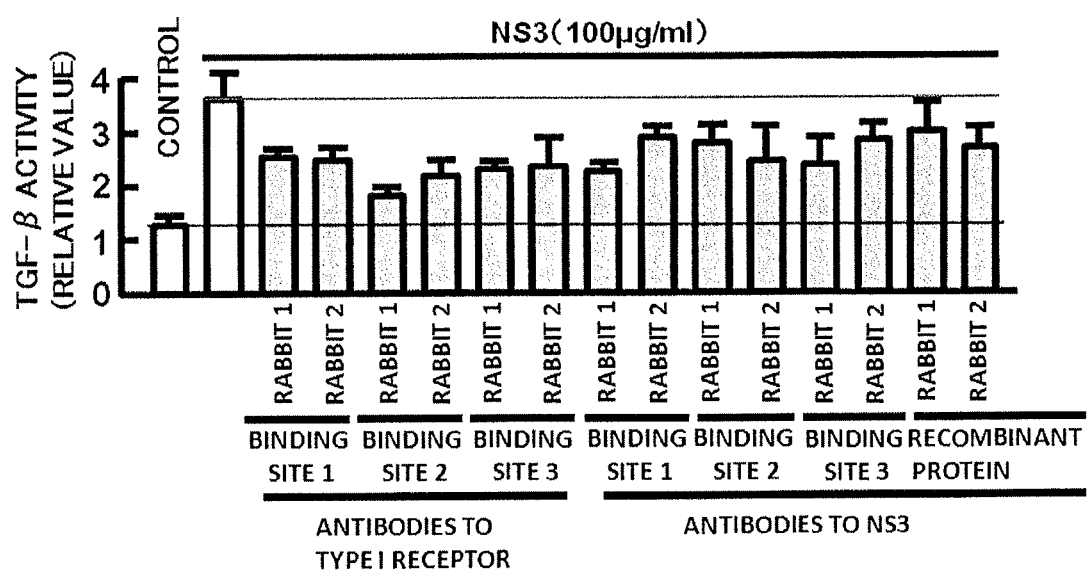
FIG. 7 is a graph showing that anti-type I TGF-β receptor antibodies and anti-NS3 antibodies which bind to the putative binding sites inhibit TGF-β signal activation due to NS3 protease, under a condition that each antibody and the NS3 protease are simultaneously added to ×9CAGA/CCL64 cells.

Examination of Inhibition of TGF-β-Like Activity of NS3 Protease by Antibodies to Binding Sites Between NS3 Protease and TGF-β Receptor In the same manner as in Example 2, the ×9CAGA/CCL64 cells were suspended at a concentration of $2 \times 10^5$ cells/ml in the culture medium, seeded in a 96-well cell culture plate at 100 μl/well, and cultured overnight at 37° C. in the presence of 5% $CO_2$. After the culturing, the culture supernatant in the plate was removed by suction, and the cells were washed with PBS(+). Then, each of "mixture solutions of the NS3 protease and an antibody" and a solution containing only the NS3 protease was added at 100 μl/well, and the cells were cultured at 37° C. in the presence of 5% $CO_2$ for additional 20 hours. Then, the reporter activity in the presence of each antibody was determined in the same manner as in Example 2. FIG. 7 shows the obtained results. Note that, in FIGS. 7 to 14, "Control" represents a value of the reporter activity of the cells cultured under the condition that neither the protein (the purified recombinant NS3 protein or recombinant human TGF-β2) nor the antibody was added to the medium, and no contact was allowed. The expressions "Rabbit 1" and "Rabbit 2" indicate that the polyclonal antibodies were extracted from different rabbits, although these rabbits were immunized with the same antigen.

Moreover, the "mixture solutions of the NS3 protease and an antibody" was prepared by adding, to the treatment medium, the purified recombinant NS3 protein at a final concentration of 100 μg/ml, and further adding thereto one of the six antibodies (hereinafter, also referred to as "anti-1-type receptor antibodies") prepared against the putative binding sites on the type I TGF-β receptor side, one of the six antibodies (hereinafter, also referred to as "anti-NS3 antibodies") prepared against the putative binding sites on the NS3 side on the NS3 protease side, or one of the two antibodies (hereinafter, also referred to as "anti-recombinant NS3 antibodies") prepared against the purified recombinant NS3 protein, at a final concentration of 10 μg/ml.

Figure 8:
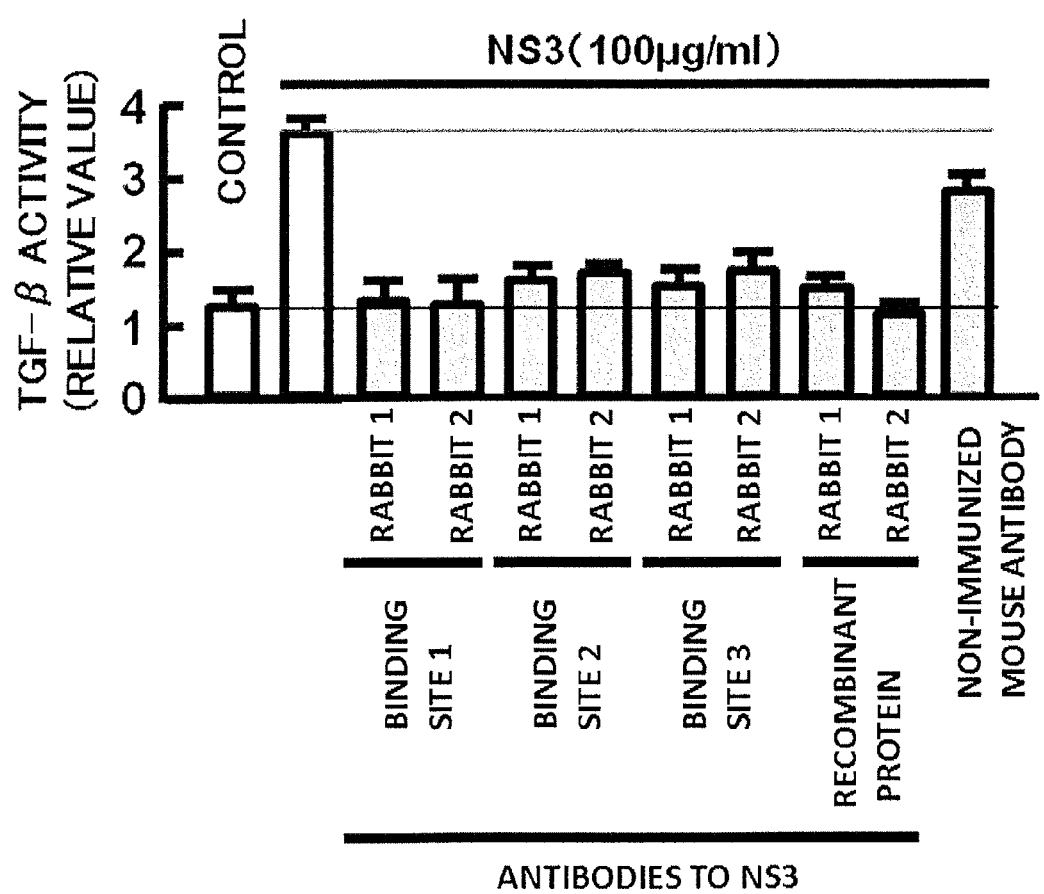
FIG. 8 is a graph showing that the anti-NS3 antibodies inhibit TGF-β signal activation due to NS3 protease, under a condition that each anti-NS3 antibody and the NS3 protease are preincubated.

Moreover, the reporter activity in the presence of each of the following antibodies was determined in the same manner as described above, except that the "mixture solutions of the NS3 protease and an antibody" used were those prepared by adding, to the treatment medium, the purified recombinant NS3 protein at a final concentration of 100 μg/ml, and further adding one of the six anti-NS3 antibodies, one of the anti-recombinant NS3 antibodies, or an antibody from a non-immunized mouse as a negative control at a final concentration of 10 μg/ml, followed by preincubation at 4° C. for 1 hour. FIG. 8 shows the obtained results.

Figure 9:
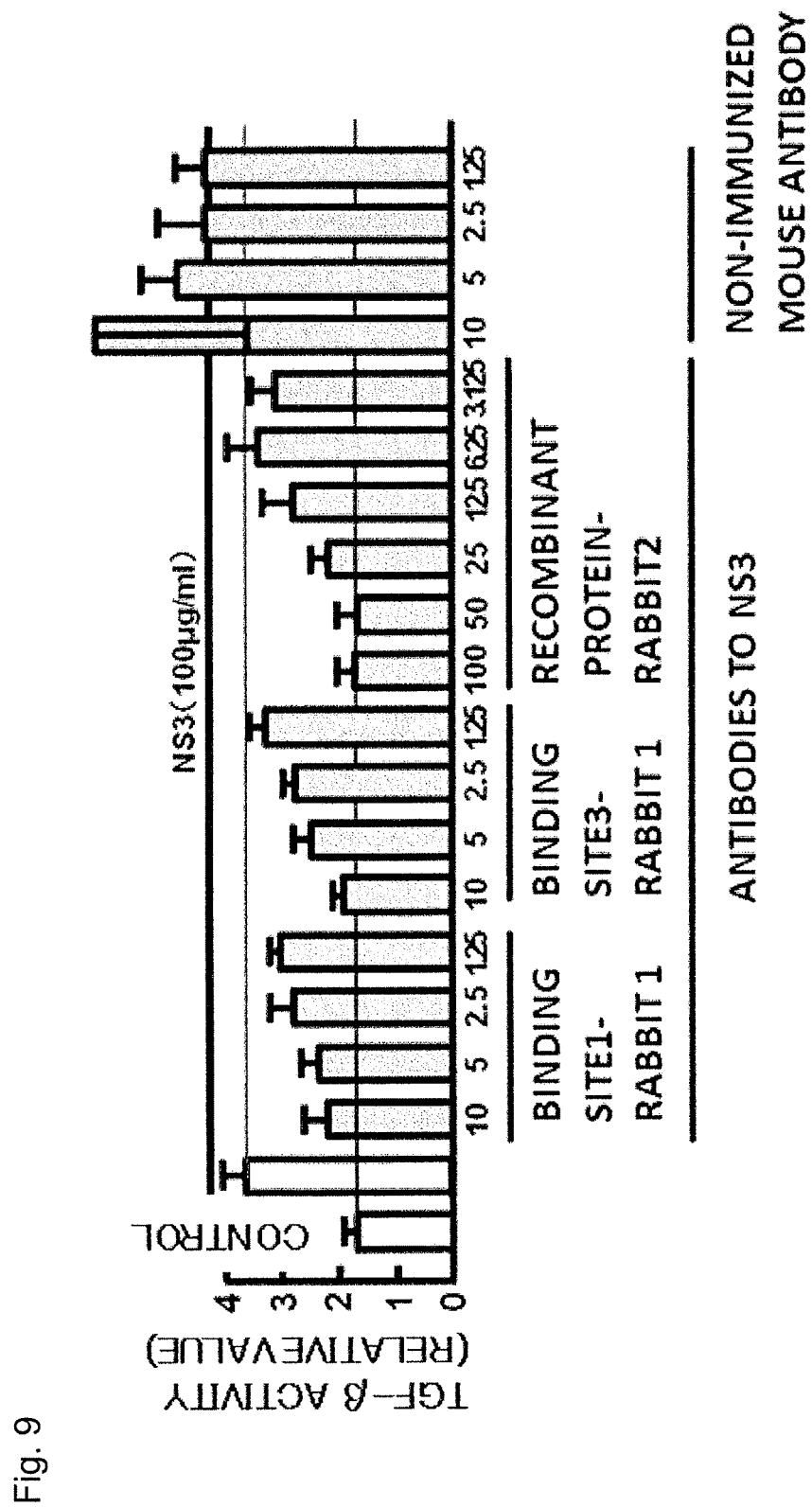
FIG. 9 is a graph showing that anti-NS3 antibodies inhibit TGF-β signal activation due to NS3 protease in a dependent manner on the dose of the antibodies, under a condition that each anti-NS3 antibody and the NS3 protease are preincubated.

Moreover, the reporter activity in the presence of each of the following antibodies was determined in the same manner as described above, except that the "mixture solutions of the NS3 protease and an antibody" used were those prepared by adding, to the treatment medium, the purified recombinant NS3 protein at a final concentration of 100 μg/ml, and further adding one of two anti-NS3 antibodies at a final concentration of 1.25, 2.5, 5, or 10 μg/ml, the anti-recombinant NS3 antibodies at a final concentration of 3.1, 6.3, 12.5, 25, 50, or 100 μg/ml, or the non-immunized mouse antibody at a final concentration of 1.25, 2.5, 5, or 10 μg/ml, followed by preincubation at 4° C. for 1 hour. FIG. 9 shows the obtained results.

Figure 10:
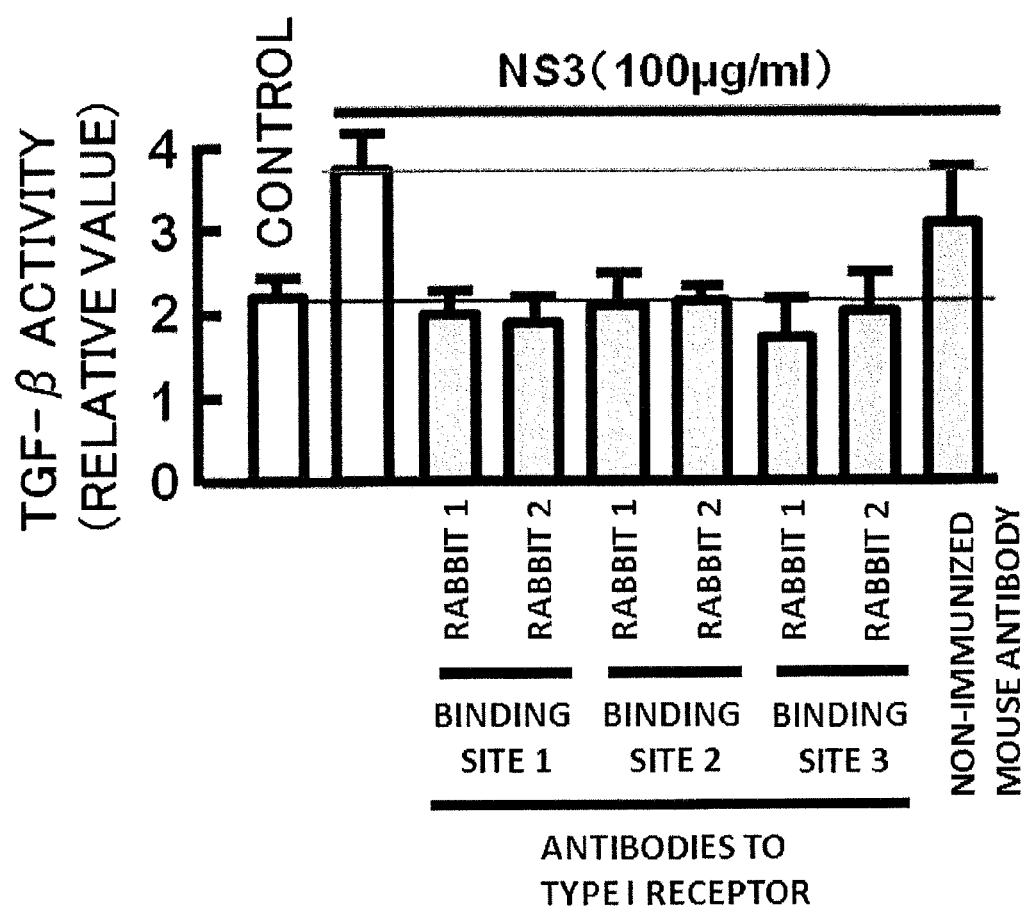
FIG. 10 is a graph showing that the anti-type I TGF-β receptor antibodies inhibit TGF-β signal activation due to NS3 protease, under a condition that each type I TGF-β receptor antibody and ×9CAGA/CCL64 cells are preincubated.

In addition, the ×9CAGA/CCL64 cells were seeded in a 96-well cell culture plate, and cultured overnight in the same manner as described above. Then, the culture supernatant in the plate was removed by suction, and the cells were washed with PBS(+). Then, to the washed cells, a treatment medium to which one of the six anti-1-type receptor antibodies or the non-immunized mouse antibody (negative control) was added at 20 μg/ml was added at 50 μl/well, and treatment was performed in the presence of 5% $CO_2$ at 37° C. for 1 hour. After that, a treatment medium to which the purified recombinant NS3 protein was added at 200 μg/ml was further added at 50 μl/well. With the final concentration of each antibody being 10 μg/ml, and with the final concentration of the purified recombinant NS3 protein being 100 μg/ml, the cells were cultured at 37° C. in the presence of 5% $CO_2$ for additional 20 hours. After the culturing, the reporter activity in the presence of each antibody was determined in the same manner as in Example 2. FIG. 10 shows the obtained results.

Furthermore, the ×9CAGA/CCL64 cells were seeded in a 96-well cell culture plate, and cultured overnight in the same manner as described above. Then, the culture supernatant in the plate was removed by suction, and the cells were washed with PBS(+). Then, to the washed cells, a treatment medium to which one of two anti-I-type receptor antibodies or the non-immunized mouse antibody (negative control) was added at 2.5, 5, 10, or 20 μg/ml was added at 50 μl/well, and treatment was performed in the presence of 5% $CO_2$ at 37° C. for 1 hour. After that, a treatment medium to which the purified recombinant NS3 protein was added at 200 μg/ml was further added at 50 μl/well. With the final concentration of each antibody being 1.25, 2.5, 5, or 10 μg/ml, and with the final concentration of the purified recombinant NS3 protein being 100 μg/ml, the cells were cultured at 37'C in the presence of 5% $CO_2$ for additional 20 hours. After the culturing, the reporter activity in the presence of each antibody was determined in the same manner as in Example 2. FIG. 11 shows the obtained results.

As is apparent from the results shown in FIG. 7, it was found that the simultaneous additions of the NS3 protease with the six anti-I-type receptor antibodies, the six anti-NS3 antibodies, and the two anti-recombinant NS3 antibodies to the cells inhibited the increase in luciferase activity due to NS3 protease by 30 to 50%.

Moreover, as is apparent from the results shown in FIGS. 8 and 10, it was found that the pretreatment of each antigen with the corresponding antibody resulted in almost 100% inhibition of the increase in luciferase activity due to NS3 protease.

Furthermore, the concentration dependence of the antibodies having high inhibition effects was examined. As is apparent from the results shown in FIGS. 9 and 11, it was found that the antibodies inhibited the increase in luciferase activity due to NS3 protease in a concentration dependent manner.

Moreover, as is apparent from the results shown in FIGS. 7 to 11, such an inhibition action was not observed by the non-immunized mouse antibody used as the negative control. These results have revealed that the NS3 protease binds to the type I TGF-β receptor at the putative sites found in Example 4 to activate the TGF-β signal.

Moreover, the results of experiments using such antibodies have demonstrated that the NS3 protease and the type I TGF-β receptor bind to each other actually through the putative binding sites, resulting in the activation of TGF-β receptors due to NS3 protease. It was also shown that the antibodies recognizing the putative binding sites in the NS3 protease or the type I TGF-β receptor also inhibited the activation of TGF-β receptors due to NS3 protease. These results, in combination with the results described in Example 3, have revealed that the antibody of the present invention is effective for preventing or treating a liver disease caused by hepatitis C virus.

Example 7

Figure 12:
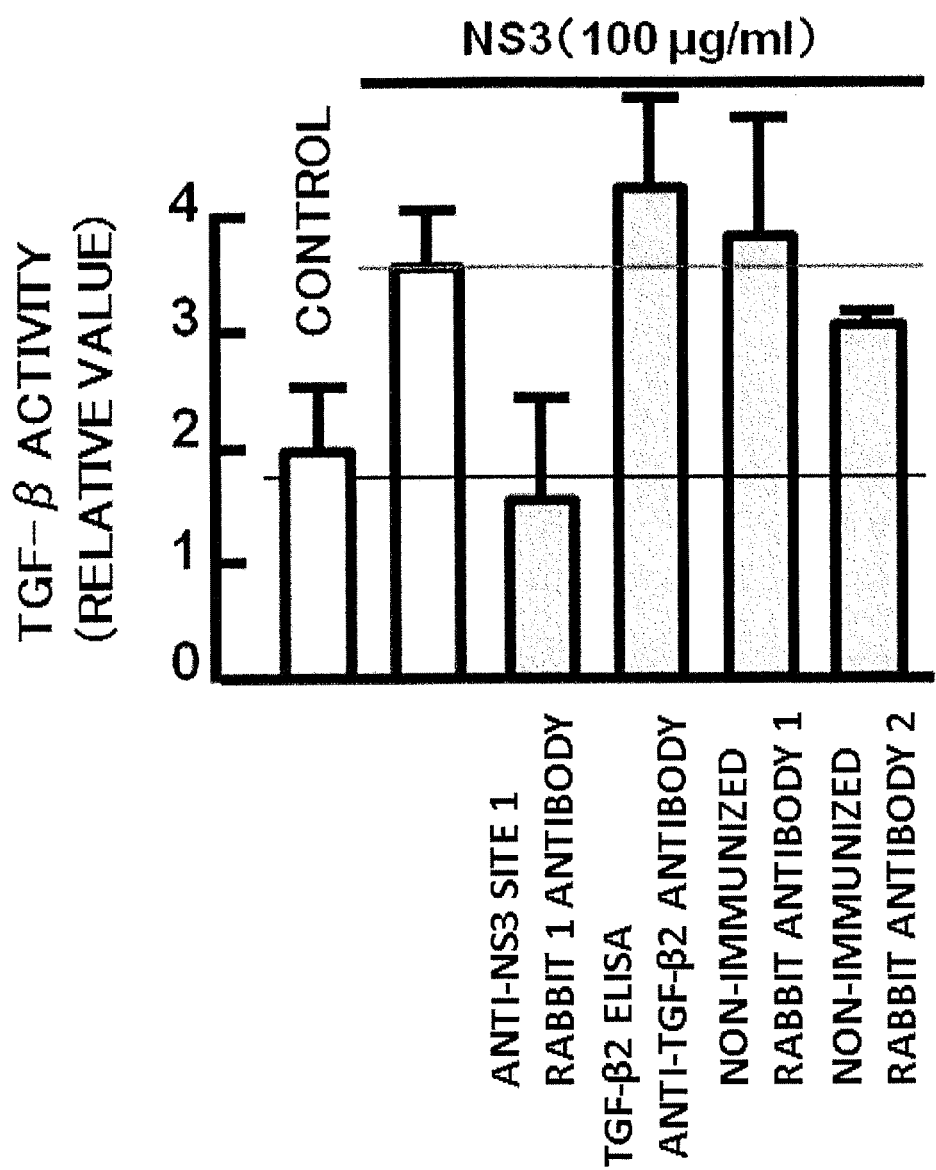
FIG. 12 is a graph showing that an anti-TGF-β2 antibody and the like which do not recognize any of the putative binding sites do not inhibit TGF-β signal activation due to NS3 protease.

Examination of Specificity of Luciferase Activity Inhibition Effect Caused by Antibody to Binding Site Between NS3 Protease and TGF-β Receptor The x9CAGA/CCL64 cells were seeded in a 96-well cell culture plate, and cultured overnight in the same manner as in Example 2. Treatment media were prepared to which the purified recombinant NS3 protein was added at a final concentration of 100 μg/ml, and to which an anti-NS3 antibody, the anti-TGF-β2 polyclonal antibody included in TGF-β2 Emax(R) ImmunoAssay System (manufactured by Promega), or one of two non-immunized rabbit antibodies was added at a final concentration of approximately 10 μg/ml. The treatment media were preincubated at 4° C. for 1 hour. Then, after the overnight culturing, the culture supernatant was removed by suction form the plate, and the plate was washed with PBS(+). Then, the preincubated treatment media were each added at 100 μl/well, and the cells were cultured at 37° C. in the presence of 5% $CO_2$ for additional 20 hours. After that, the reporter activity was determined in the presence of each antibody in the same manner as in Example 2. FIG. 12 shows the obtained results.

As is apparent from the results shown in FIG. 12, the anti-NS3 antibody achieved almost 100% inhibition of the increase in luciferase activity by the NS3 protease, whereas no such an inhibition effect was obtained by any one of the anti-TGF-β2 polyclonal antibody having affinity for NS3 protease, and the non-immunized rabbit antibodies. Hence, it has been revealed from these results that the binding to a putative site found in Example 4 is effective for inhibiting the TGF-β signal transduction due to NS3 protease.

Example 8

Figure 13:
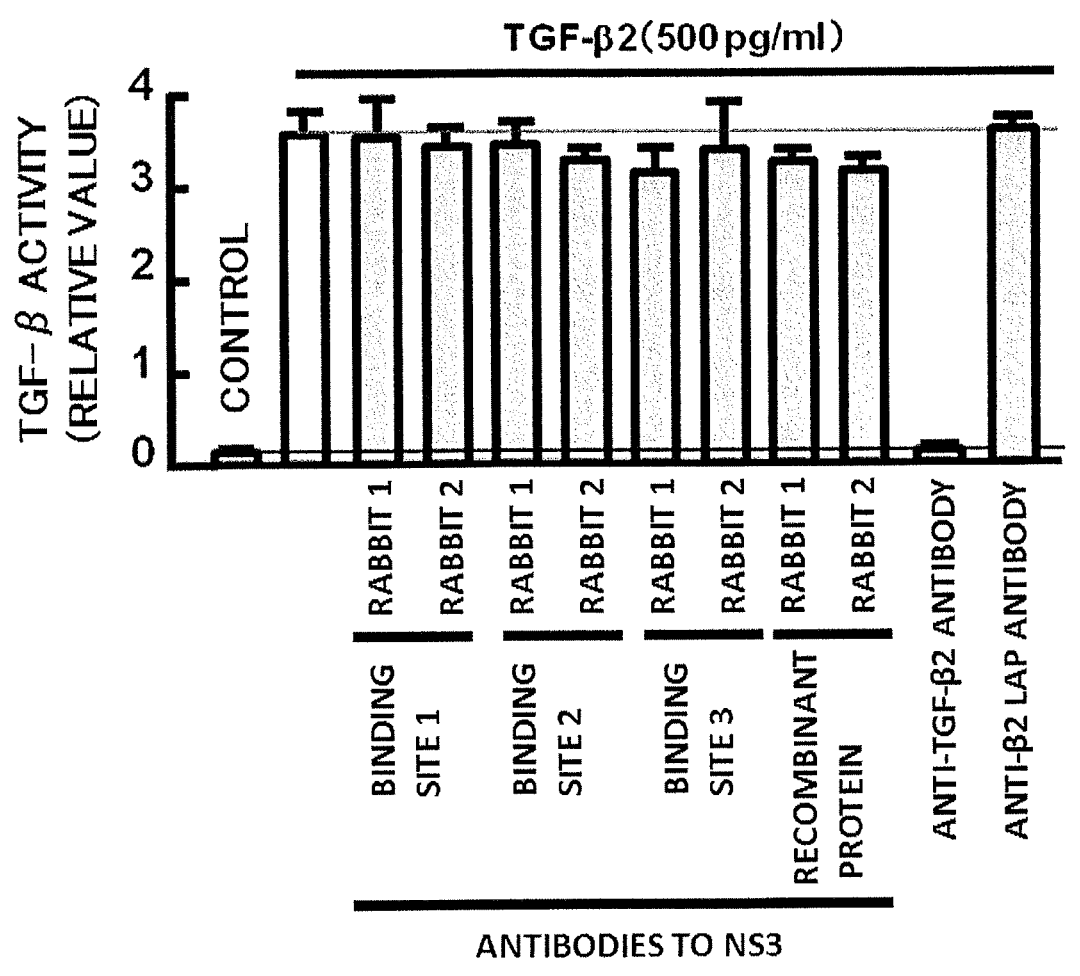

Examination of Influence of Antibodies to Binding Sites Between NS3 Protease and TCF-β Receptor on TGF-β2 Activity The x9CAGA/CCL64 cells were seeded in a 96-well cell culture plate, and cultured overnight in the same manner as in Example 2. Treatment media were prepared to which a recombinant human TGF-β2 (manufactured by PeproTech) was added at a final concentration of 500 μg/ml and to which an anti-NS3 antibody, an anti-recombinant NS3 antibody, an anti-TGF-β2 antibody as a positive control, or an anti-TGF-β2-LAP antibody as a negative control was added at a final concentration of 10 μg/ml. The treatment media were preincubated at 4° C. for 1 hour. Then, after the overnight culturing, the culture supernatant was removed from the plate by suction, and the cells were washed with PBS(+). Then, the pre-incubated treatment media were each added at 100 μl/well, and the cells were cultured at 37° C. in the presence of 5% $CO_2$ for additional 20 hours. After that, the reporter activity was determined in the presence of each antibody in the same manner as in Example 2. FIG. 13 shows the obtained results.

Figure 14:
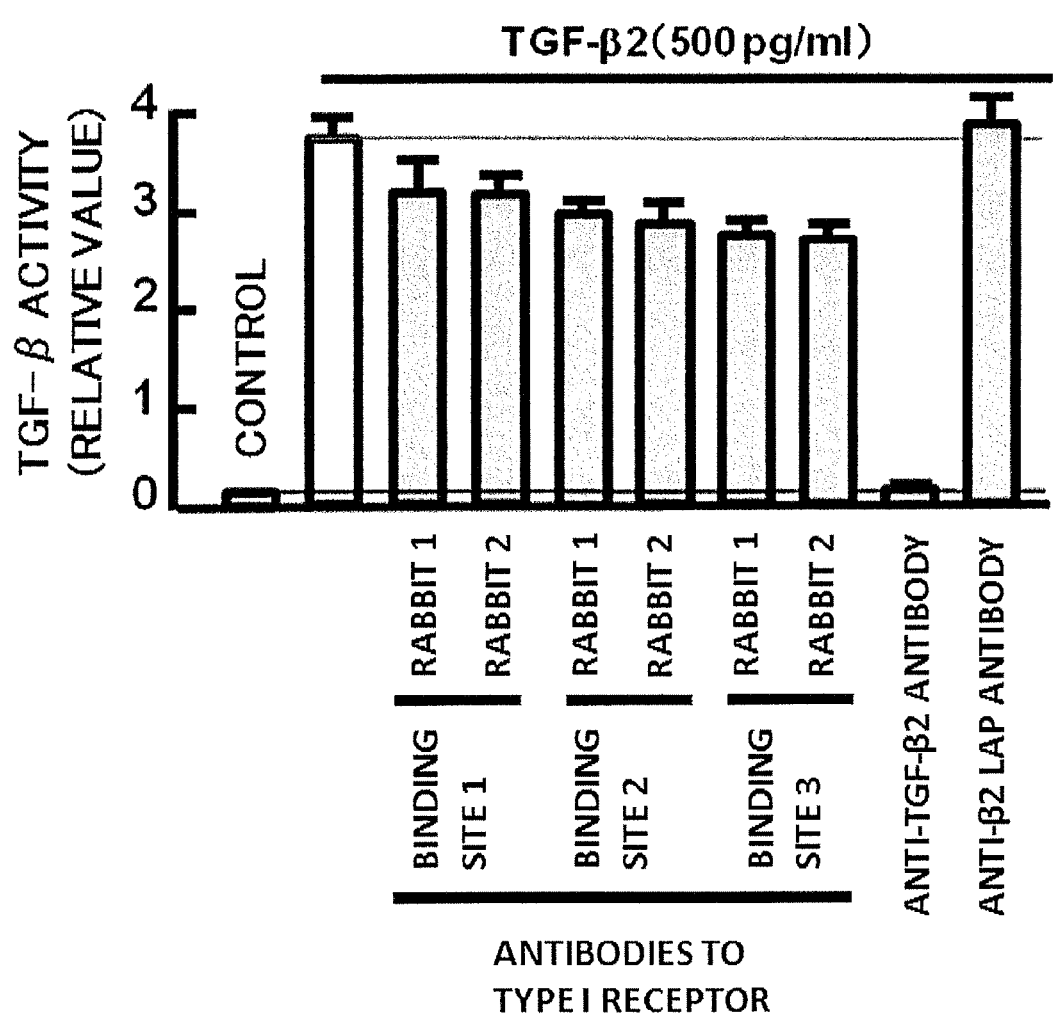
FIG. 14 is a graph showing that anti-type I TGF-β receptor antibodies partially inhibit TGF-β signal activation due to TGF-β2, under a condition that each anti-type I TGF-β receptor antibody and cells (reporter assay system) are preincubated.

Moreover, the x9CAGA/CCL64 cells were seeded in a 96-well cell culture plate, and cultured overnight in the same manner as in Example 2. After the overnight culturing, the culture supernatant was removed from the plate by suction, and the cells were washed with PBS(+). Then, treatment media each containing an anti-1-type receptor antibody, an anti-TGF-β2 antibody (positive control), or an anti-TGF-β2-LAP antibody (negative control) at a concentration of 20 μg/ml were each added at 50 μl/well, and treatment was conducted at 37° C. in the presence of 5% $CO_2$ for 1 hour. After that, a treatment medium containing 1000 pg/ml recombinant human TGF-β2 was added at 50 μl/well, and adjustment was made such that the final concentration of the recombinant human TGF-β2 was 500 μg/ml, and the final concentration of each antibody was 10 μg/ml. Then, the cells were cultured at 37° C. in the presence of 5% $CO_2$ for additional 20 hours. After that, the reporter activity was determined in the presence of each antibody in the same manner as in Example 2. FIG. 14 shows the obtained results.

As is apparent from the results shown in FIG. 13, the anti-TGF-β2 antibody, which was the positive control, inhibited the TGF-β2 activity by almost 100%, whereas no influences of the antibodies to NS3 protease on the TGF-β2 activity were observed. On the other hand, as is apparent from the results shown in FIG. 14, the TGF-β2 activity was inhibited by the antibodies to type I TGF-β receptor by 27% at the maximum. Hence, it has been suggested from these results that although the binding sites between the NS3 protease and the TGF-β receptor are not completely the same as the binding sites between TGF-β2 and the TGF-β receptor, some portions are shared by these binding sites.

Example 9

Preparation of Monoclonal Antibodies to Binding Sites between NS3 Protease and TGF-β Receptor <Purification of NS3 Protein for Preparing Monoclonal Antibodies>

First, a plasmid vector pET32a(+) into which a gene encoding scNS4A-NS3 protease was inserted was incorporated into *Escherichia coli* strain KRX into which pMINOR plasmid was introduced, and the *E. coli* was cultured. Note that, for the scNS4A-NS3 protease, see Protein Sci., 1998, Vol. 7, No. 10, pp. 2143 to 2149. Meanwhile, for the pMINOR plasmid, see J. Struct. Func. Genom., 2006, vol. 7, pp. 31 to 36.

Then, after the expression of the target protein was induced by rhamnose, the culture liquid of the *E. coli* in which the expression of the protein was induced was centrifuged to collect the bacterial cells. The collected bacterial cells were suspended in a buffer (20 mM Tris-HCl [pH 8.0], 500 mM NaCl, 4 mM $MgCl_2$, 10% glycerol, 20 μM $ZnCl_2$. 1 mM DTT, 0.1% n-ctyl-β-o-glucopyranoside, complete EDTA free (manufactured by Roche Applied Science)), and the bacterial cells were disrupted by sonication. Then, the supernatant was collected by centrifugation at 14,000×g for 20 minutes. The collected supernatant was passed through a HisTrap HP column (manufactured by GE Healthcare), so that the target protein was once adsorbed onto the resin packed in the column. Then, the target protein was eluted from the resin with an elution buffer (500 mM imidazole, 20 mM Tris-HCl pH 8.0, 500 mM NaCl, 20 μM $ZnCl_2$, and 1 mM DTT).

The thus obtained eluate was passed through a HiPrep 26/60 Desalting column (manufactured by GE Healthcare) to perform a desalination operation and buffer exchange, so that a buffer (20 mM Tris-HCl [pH 8.0], 150 mM NaCl, 20 μM $ZnCl_2$, 10 mM DTT, and 100 mM $CaCl_2$) containing the target protein was obtained. This buffer containing the target protein was passed through an EndoTrap Blue column (manufactured by Hyglos GmbH) to remove endotoxin, and the filtrate was collected, and used as an NS3 protein (hereinafter, also referred to as "recombinant NS3") for monoclonal antibody preparation in the following experiments.

<Immunization and Cell Fusion>

Next, female BALB/c mice were immunized with the recombinant NS3 by intraperitoneal injection. For the initial immunization, 50 μg of the recombinant NS3 in Freund's complete adjuvant was administered to each mouse. For the following immunizations, 50 μg of the recombinant NS3 in an O/W emulsion adjuvant was administered. The immunization was performed every three weeks. The final immunization was performed by administering phosphate buffered saline (PBS) containing 50 μg of the recombinant NS3. Three days after the final immunization, spleen cells of mice with high serum antibody titers were subjected to a cell fusion treatment with P3.X63-Ag8.653 mouse myeloma cells by using polyethylene glycol 4000. The hybridoma cells were selected by using the known Kohler and Milstein technique in an HAT medium.

Note that the serum antibody titer was assayed by the ELISA method. In this assay, first, a 96-well microplate was coated with the recombinant NS3 or one of Imject OVA-bound antigens, which will be described later, (hereinafter, the antigens are also referred to as "OVA-bound synthetic peptides"). Subsequently, blocking was performed with 1% skimmed milk/phosphate buffered saline, and then the serum, serially diluted, was added, followed by incubation. The plate was washed with TBS/0.05% Tween 20, and then a peroxidase-conjugated antibody to mouse immunoglobulin diluted with 1% skimmed milk/phosphate buffered saline was added to the wells, followed by incubation at room temperature for 1 hour. After the incubation, the plate was washed with TBS/0.05% Tween 20. A substrate solution (0.05% o-phenylenediamine/citrate buffer (pH 5)/0.03% $H_2O_2$) was added to the wells, and a chromogenic reaction was performed. Ten minutes after the addition of the substrate solution, the reaction was stopped by adding 2 N sulfuric acid, and the absorbance at 490 nm was measured with a spectrophotometer.

<Preparation of OVA-Bound Synthetic Peptides>

First, the peptides NS-1 to NS-3 (BIO MATRIX RESEARCH, INC.) shown in Table 1 were synthesized by the Fmoc solid-phase synthesis method. The final peptide products were prepared by deprotection and cleavage from the resin with a cleavage cocktail containing 95% TFA. In addition, Imject OVA (manufactured by Thermo SCIENTIFIC Pierce Protein Research Products) was bound as a carrier protein to each synthetic peptide for the purpose of using the synthetic peptide in screening.

<Screening>

Hybridomas which reacted with the recombinant NS3 were selected by an ELISA method and an immunoprecipitation-ELISA method based on immunoprecipitation. Specifically, first, the recombinant NS3 (prepared at a final concentration of 1 μg/mL with a 50 mM carbonate buffer) was immobilized to a hydrophobic/hydrophilic molecule-adsorbing 96-well microplate at room temperature in 1 hour. Subsequently, the plate was washed with TBS/0.05% Tween 20, then free adsorption sites on the surfaces of the wells were blocked by using 1% skimmed milk/phosphate buffered saline at room temperature in 1 hour, and then the plate was washed again with TBS/0.05% Tween 20. Hybridoma culture supernatants were added to the wells, followed by incubation at room temperature for 1 hour. After that, the plate was washed with TBS/0.05% Tween 20, and subsequently a peroxidase-conjugated mouse anti-IgG antibody diluted with 1% skimmed milk/phosphate buffered saline was added to the wells, followed by incubation at room temperature for 1 hour. After the incubation, the plate was washed with TBS/0.05% Tween 20. A substrate solution (0.05% o-phenylenediamine/citrate buffer (pH 5)/0.03% $H_2O_2$) was added to the wells, and a chromogenic reaction was performed. Ten minutes after the addition of the substrate solution, the reaction was stopped with 2 N sulfuric acid, and the absorbance at 490 nm was measured with a spectrophotometer. In addition, for comparison, the anti-NS1 peptide polyclonal antibody (the polyclonal antibody which was prepared in Example 5 and which binds to NS-1 shown in Table 1), the anti-NS3 peptide polyclonal antibody (the polyclonal antibody which was prepared in Example 5 and which binds to NS-3 shown in Table 1), and the anti-riken NS3 peptide polyclonal antibody (the polyclonal antibody which was prepared in Example 5 and whose antigen was the purified recombinant NS3 protein) were evaluated in the same manner (hereinafter, the same shall apply). The obtained results are shown in Columns C of Tables 2 and 3.

Meanwhile, in the immunoprecipitation-ELISA, reaction liquids each obtained by mixing the recombinant NS3, antibody adsorption beads, and one of solutions of the hybridoma culture supernatants were stirred for 1 hour, and then allowed to stand for 5 minutes. The obtained supernatants were used as samples and assayed by an ELISA method. The obtained results are shown in Columns B of Tables 2 and 3. Note that each "IP %" shown in Columns B of Tables 2 and 3 is a value calculated with a value measured by the ELISA method for the supernatant in which the antigen was completely removed by the antibody being regarded as 100%, and with a value measured by the ELISA method for the supernatant in which the antigen was not removed at all being regarded as 0%.

TABLE 2

| No. | Clone # | Iso type | A Reporter assay 1 μg/mL (Binding inhibition %) | A Reporter assay 0.1 μg/mL (Binding inhibition %) | B CELIXSYS 1 μg/mL (IP %) | B CELIXSYS 0.1 μg/mL (IP %) | C Riken NS3 antigen Ag-ELISA 1 μg/mL ($OD_{490}$ nm) | C Riken NS3 antigen Ag-ELISA 0.1 μg/mL ($OD_{490}$ nm) | D ALEXIS NS3 antigen Ag-ELISA 1 μg/mL ($OD_{490}$ nm) | D ALEXIS NS3 antigen Ag-ELISA 0.1 μg/mL ($OD_{490}$ nm) |
|---|---|---|---|---|---|---|---|---|---|---|
| 1 | e1211 | IgG2a | 59.0 | 22.2 | 83.4 | 42.2 | 2.33 | 1.50 | 1.22 | 0.29 |
| 2 | P3-g1390 | IgG1 | 52.2 | 5.9 | 56.4 | 21.4 | 1.41 | 0.94 | 0.28 | 0.12 |
| 3 | s0647 | IgG2a | 48.1 | 26.7 | 84.5 | 56.0 | 2.42 | 2.16 | 0.11 | 0.09 |
| 4 | P3-g0948 | IgG3 | 35.7 | 30.3 | 88.1 | 51.5 | 1.26 | 1.03 | 0.08 | 0.07 |
| 5 | P3-g0899 | IgG2a | 35.6 | 16.5 | 81.7 | 26.0 | 1.96 | 0.91 | 0.54 | 0.14 |
| 6 | P3-g1651 | IgG3 | 33.0 | 1.9 | 93.4 | 66.2 | 1.27 | 1.12 | 0.35 | 0.25 |
| 7 | e0458 | IgG2a | 30.4 | 30.9 | 62.5 | 24.4 | 2.31 | 1.32 | 0.07 | 0.07 |
| 8 | b0523 | IgG2a | 27.4 | 22.2 | 20.6 | 20.4 | 0.49 | 0.13 | 0.09 | 0.08 |
| 9 | P3-g1421 | IgG3 | 27.1 | 28.2 | 93.4 | 34.6 | 2.63 | 1.44 | 0.12 | 0.09 |
| 10 | c1480 | IgG2a | 26.2 | 15.5 | 86.8 | 55.2 | 2.24 | 2.05 | 1.03 | 0.61 |
| 11 | b0828 | IgG2a | 26.1 | 28.9 | 79.5 | 31.5 | 2.42 | 1.92 | 0.11 | 0.07 |
| 12 | P3-g1341 | IgG2a | 22.3 | 25.4 | 29.3 | 17.5 | 1.78 | 0.82 | 0.40 | 0.12 |
| 13 | P3-g0947 | IgG3 | 20.9 | 11.5 | 85.4 | 51.2 | 1.02 | 0.63 | 0.22 | 0.10 |
| 14 | c0320 | IgG2b | 20.5 | 0.0 | 57.5 | 10.2 | 2.29 | 0.96 | 0.06 | 0.09 |
| 15 | c0198 | IgG2a | 20.1 | 0.0 | 49.8 | 11.4 | 2.18 | 0.68 | 0.71 | 0.15 |
| 16 | b1195 | IgG2a | 18.2 | 9.5 | 78.2 | 31.1 | 2.31 | 1.77 | 0.07 | 0.08 |
| 17 | P3-g1649 | IgG2a | 15.8 | 7.0 | 78.0 | 31.6 | 1.50 | 0.62 | 0.23 | 0.09 |
| 18 | P3-g0979 | IgG3 | 13.1 | 13.6 | 83.6 | 42.3 | 0.47 | 0.26 | 0.12 | 0.08 |
| 19 | c0319 | IgG1 | 12.7 | 0.0 | 7.7 | 12.8 | 0.05 | 0.05 | 0.07 | 0.06 |
| 20 | b0733 | IgG2a | 11.6 | 22.2 | 41.2 | 25.6 | 2.29 | 1.50 | 0.07 | 0.07 |
| 21 | c1531 | IgG2a | 10.1 | 8.0 | 74.4 | 15.6 | 2.41 | 1.44 | 0.07 | 0.08 |
| 22 | P3-g0811 | IgG3 | 8.0 | 0.0 | 55.5 | 16.9 | 1.00 | 0.33 | 0.19 | 0.08 |

TABLE 3

| No. | Clone # | Iso type | A Reporter assay 1 μg/mL (Binding inhibition %) | A Reporter assay 0.1 μg/mL (Binding inhibition %) | B CELIXSYS 1 μg/mL (IP %) | B CELIXSYS 0.1 μg/mL (IP %) | C Riken NS3 antigen Ag-ELISA 1 μg/mL ($OD_{490}$ nm) | C Riken NS3 antigen Ag-ELISA 0.1 μg/mL ($OD_{490}$ nm) | D ALEXIS NS3 antigen Ag-ELISA 1 μg/mL ($OD_{490}$ nm) | D ALEXIS NS3 antigen Ag-ELISA 0.1 μg/mL ($OD_{490}$ nm) |
|---|---|---|---|---|---|---|---|---|---|---|
| 23 | P3-g1135 | IgG2a | 7.5 | 0.0 | 77.7 | 27.2 | 2.10 | 1.09 | 0.22 | 0.10 |
| 24 | c1594 | IgG2a | 6.6 | 0.0 | 85.7 | 21.8 | 2.48 | 1.80 | 0.95 | 0.31 |
| 25 | P3-g0977 | IgG3 | 2.1 | 5.4 | 91.8 | 68.0 | 1.42 | 1.18 | 0.42 | 0.26 |
| 26 | P3-g1402 | IgG1 | 0.6 | 0.0 | 49.9 | 27.9 | 1.33 | 0.57 | 0.14 | 0.08 |
| 27 | c0346 | IgG2a | 0.0 | 0.0 | 85.4 | 16.5 | 2.37 | 1.40 | 0.06 | 0.08 |
| 28 | c0569 | IgG2a | 0.0 | 0.0 | 8.1 | 17.0 | 0.05 | 0.05 | 0.06 | 0.05 |
| 29 | e1268 | IgG2a | 0.0 | 0.0 | 48.8 | 47.8 | 0.07 | 0.07 | 0.09 | 0.07 |
| 30 | P3-g1005 | IgG2a | 0.0 | 0.0 | 51.5 | 19.4 | 1.64 | 0.61 | 0.08 | 0.07 |
| 31 | s1314 | IgG2a | 0.0 | 16.6 | 75.3 | 54.1 | 1.93 | 0.53 | 0.10 | 0.09 |
| 32 | e1309 | IgG1 | 48.0 | 13.7 | 16.6 | 20.5 | 0.06 | 0.05 | 0.10 | 0.06 |
| 33 | b0248 | IgG1 | 36.0 | 13.5 | 18.3 | 11.2 | 0.06 | 0.06 | 0.09 | 0.06 |
| 34 | k0228 | IgM | 36.4 | 36.7 | 55.2 | 43.6 | 0.06 | 0.06 | 0.08 | 0.08 |
| 35 | e1359 | IgM | 30.3 | 11.8 | 44.8 | −16.8 | 0.06 | 0.06 | 0.09 | 0.07 |
| — | Anti-NS1 peptide polyclonal antibody | N.A. | 41.6 | 26.8 | 28.7 | 21.0 | 0.90 | 0.17 | 0.14 | 0.11 |
| — | Anti-NS3 peptide polyclonal antibody | N.A. | 32.0 | 22.5 | 18.8 | 13.8 | 0.34 | 0.07 | 0.07 | 0.07 |
| — | Anti-riken NS3 peptide polyclonal antibody | N.A. | 12.4 | 14.3 | 11.7 | 10.1 | 0.81 | 0.14 | 0.07 | 0.07 |

Next, in order to exclude hybridomas which reacted with a tag protein (trx-His-S tag) contained in the recombinant NS3, selection was performed by an ELISA method and by an immunoprecipitation-ELISA method based on immunoprecipitation, while the reactivity with a recombinant trx-His-S tag protein prepared from recombinant *E. coli* was employed as an index. Specifically, first, the trx-His-S tag protein (prepared at a final concentration of 1 μg/mL with a 50 mM carbonate buffer) was immobilized to a hydrophobic/hydrophilic molecule-adsorbing 96-well microplate at room temperature in 1 hour. Subsequently, the plate was washed with TBS/0.05% Tween 20, then free adsorption sites on surfaces of the wells were block by using 1% skimmed milk/phosphate buffered saline at room temperature in 1 hour, and the plate was washed again with TBS/0.05% Tween 20. Hybridoma culture supernatants were added to the wells, and incubated at room temperature for 1 hour. After that, the plate was washed with TBS/0.05% Tween 20. Subsequently, a peroxidase-conjugated mouse anti-IgG antibody diluted with 1% skimmed milk/phosphate buffered saline was added to the wells, followed by incubation at room temperature for 1 hour. After the incubation, the plate was washed with TBS/0.05% Tween 20. A substrate solution (0.05% o-phenylenediamine/citrate buffer (pH 5)/0.03% $H_2O_2$) was added to the wells, and a chromogenic reaction was performed. Ten minutes after the addition of the substrate solution, the reaction was stopped with 2 N sulfuric acid, and the absorbance at 490 nm was measured with a spectrophotometer.

Meanwhile, in the immunoprecipitation-ELISA method, reaction liquids each obtained by mixing the trx-His-S tag protein, antibody adsorption beads, and one of solutions of the hybridoma culture supernatants were stirred for 1 hour. The obtained supernatants were used as samples, and assayed by an ELISA method.

Then, hybridomas found to show a reactivity with the Trx-His-Stag protein in the ELISA method and the immunoprecipitation-ELISA method using the trx-His-S tag protein were excluded from the subjects of the examination, because these hybridomas were presumably clones producing an anti-trx-His-S tag protein antibody.

<Study on Epitopes>

Hybridomas positive for the recombinant NS3 selected by the above-described methods were investigated by an ELISA method for the reactivities of the anti-NS3 monoclonal antibodies, which were produced by these hybridomas, with the synthetic peptides (NS-1 to NS-3), and epitopes recognized by these antibodies were studied. Specifically, first, the OVA-bound NS-1, NS-2, and NS-3 synthetic peptides (each prepared at a final concentration of 0.5 μg/mL with a 50 mM carbonate buffer) were each immobilized to a hydrophobic/hydrophilic molecule-adsorbing 96-well microplate at room temperature in 1 hour. Subsequently, the plate was washed with TBS/0.05% Tween 20, then free adsorption sites on surfaces of the wells were blocked by using 1% skimmed milk/phosphate buffered saline at room temperature in 1 hour, and the plate was again washed with TBS/0.05% Tween 20. Then, hybridoma culture supernatants were added to wells, and incubated at room temperature for 1 hour. After that, the plate was washed with TBS/0.05% Tween 20. Subsequently, a peroxidase-conjugated mouse anti-IgG antibody diluted with 1% skimmed milk/phosphate buffered saline was added to the wells, followed by incubation at room temperature for 1 hour. After the incubation, the plate was washed with TBS/0.05% Tween 20. A substrate solution (0.05% o-phenylenediamine/citrate buffer (pH 5)/0.03% $H_2O_2$) was added to the wells, and a chromogenic reaction was performed. Ten to fifteen minutes after the addition of the substrate solution, the reaction was stopped by adding 2 N sulfuric acid, and the absorbance at 490 nm was measured with a spectrophotometer. The obtained results are shown in Columns E to G of Tables 4 and 5.

TABLE 4

| | | | E NS1 peptide-ELISA | | F NS2 peptide-ELISA | | G NS3 peptide-ELISA | |
|---|---|---|---|---|---|---|---|---|
| | | | Antibody concentration | | | | | |
| No. | Clone # | Iso type | 1 μg/mL ($OD_{490}$ nm) | 0.1 μg/mL ($OD_{490}$ nm) | 1 μg/mL ($OD_{490}$ nm) | 0.1 μg/mL ($OD_{490}$ nm) | 1 μg/mL ($OD_{490}$ nm) | 0.1 μg/mL ($OD_{490}$ nm) |
| 1 | e1211 | IgG2a | 0.06 | 0.07 | 0.06 | 0.07 | 2.58 | 1.98 |
| 2 | P3-g1390 | IgG1 | 0.06 | 0.05 | 0.05 | 0.05 | 2.20 | 2.05 |
| 3 | s0647 | IgG2a | 0.06 | 0.07 | 2.52 | 2.10 | 0.06 | 0.06 |
| 4 | P3-g0948 | IgG3 | 0.05 | 0.05 | 0.05 | 0.05 | 2.12 | 1.49 |
| 5 | P3-g0899 | IgG2a | 0.06 | 0.05 | 0.05 | 0.05 | 2.41 | 1.44 |
| 6 | P3-g1651 | IgG3 | 0.06 | 0.07 | 0.07 | 0.07 | 2.23 | 1.62 |
| 7 | e0458 | IgG2a | 0.05 | 0.04 | 2.39 | 1.68 | 0.05 | 0.05 |
| 8 | b0523 | IgG2a | 0.06 | 0.06 | 0.06 | 0.07 | 0.06 | 0.08 |
| 9 | P3-g1421 | IgG3 | 0.07 | 0.06 | 1.99 | 0.37 | 2.07 | 1.02 |
| 10 | c1480 | IgG2a | 0.06 | 0.08 | 0.06 | 0.06 | 0.06 | 0.06 |
| 11 | b0828 | IgG2a | 0.05 | 0.05 | 2.50 | 1.95 | 0.05 | 0.06 |
| 12 | P3-g1341 | IgG2a | 0.05 | 0.05 | 0.05 | 0.06 | 2.31 | 1.91 |
| 13 | P3-g0947 | IgG3 | 0.06 | 0.05 | 0.06 | 0.05 | 2.18 | 1.48 |
| 14 | c0320 | IgG2b | 0.06 | 0.05 | 2.27 | 0.47 | 0.05 | 0.05 |
| 15 | c0198 | IgG2a | 0.05 | 0.05 | 0.06 | 0.07 | 0.06 | 0.05 |
| 16 | b1195 | IgG2a | 0.05 | 0.07 | 2.48 | 1.96 | 0.05 | 0.07 |
| 17 | P3-g1649 | IgG2a | 0.05 | 0.05 | 0.05 | 0.05 | 2.43 | 1.71 |
| 18 | P3-g0979 | IgG3 | 0.05 | 0.05 | 0.05 | 0.05 | 2.10 | 1.51 |
| 19 | c0319 | IgG1 | 0.05 | 0.05 | 0.05 | 0.05 | 0.05 | 0.06 |
| 20 | b0733 | IgG2a | 0.05 | 0.05 | 2.48 | 1.67 | 0.05 | 0.05 |
| 21 | c1531 | IgG2a | 0.06 | 0.06 | 2.53 | 0.90 | 0.05 | 0.06 |
| 22 | P3-g0811 | IgG3 | 0.06 | 0.05 | 0.05 | 0.05 | 1.53 | 0.36 |

TABLE 5

| No. | Clone # | Iso type | E NS1 peptide-ELISA Antibody concentration | | F NS2 peptide-ELISA | | G NS3 peptide-ELISA | |
|---|---|---|---|---|---|---|---|---|
| | | | 1 μg/mL (OD$_{490}$ nm) | 0.1 μg/mL (OD$_{490}$ nm) | 1 μg/mL (OD$_{490}$ nm) | 0.1 μg/mL (OD$_{490}$ nm) | 1 μg/mL (OD$_{490}$ nm) | 0.1 μg/mL (OD$_{490}$ nm) |
| 23 | P3-g1135 | IgG2a | 0.06 | 0.06 | 0.05 | 0.06 | 2.37 | 1.58 |
| 24 | c1594 | IgG2a | 0.05 | 0.05 | 2.60 | 1.63 | 0.06 | 0.05 |
| 25 | P3-g0977 | IgG3 | 0.05 | 0.05 | 0.05 | 0.05 | 2.33 | 1.71 |
| 26 | P3-g1402 | IgG1 | 0.05 | 0.05 | 0.05 | 0.05 | 2.11 | 1.03 |
| 27 | c0346 | IgG2a | 0.06 | 0.05 | 2.51 | 0.97 | 0.05 | 0.05 |
| 28 | c0569 | IgG2a | 0.05 | 0.05 | 0.05 | 0.05 | 0.05 | 0.06 |
| 29 | e1268 | IgG2a | 0.08 | 0.07 | 0.07 | 0.07 | 0.07 | 0.06 |
| 30 | P3-g1005 | IgG2a | 0.06 | 0.06 | 0.06 | 0.06 | 2.56 | 1.49 |
| 31 | s1314 | IgG2a | 0.06 | 0.08 | 1.66 | 0.29 | 0.06 | 0.06 |
| 32 | e1309 | IgG1 | 0.06 | 0.05 | 0.07 | 0.06 | 0.06 | 0.05 |
| 33 | b0248 | IgG1 | 0.06 | 0.06 | 0.06 | 0.06 | 0.07 | 0.05 |
| 34 | k0228 | IgM | 0.05 | 0.07 | 0.06 | 0.05 | 0.06 | 0.06 |
| 35 | e1359 | IgM | 0.07 | 0.06 | 0.07 | 0.05 | 0.06 | 0.06 |
| — | Anti-NS1 peptide polyclonal antibody | N.A. | 1.82 | 0.46 | 0.06 | 0.06 | 0.07 | 0.06 |
| — | Anti-NS3 peptide polyclonal antibody | N.A. | 0.06 | 0.06 | 0.08 | 0.05 | 0.94 | 0.22 |
| — | Anti-riken NS3 peptide polyclonal antibody | N.A. | 0.05 | 0.05 | 0.13 | 0.06 | 0.05 | 0.05 |

<Evaluation of Reactivities of Anti-NS3 Monoclonal Antibodies>

Moreover, the hybridomas positive for the recombinant NS3 were investigated by the ELISA method also for reactivities of the anti-NS3 monoclonal antibodies, which were produced by these hybridomas, with a NS3 peptide (commercially available product). Specifically, first, NS3-NS4A (HCV), (recombinant) (His-tag) (manufactured by ALEXIS) (prepared at a final concentration of 0.5 μg/mL with a 50 mM carbonate buffer) was immobilized to a hydrophobic/hydrophilic molecule-adsorbing 96-well microplate at room temperature in 1 hour. Subsequently, the plate was washed with TBS/0.05% Tween 20, then free adsorption sites on surfaces of the wells were blocked with 1% skimmed milk/phosphate buffered saline at room temperature in 1 hour, and the plate was again washed with TBS/0.05% Tween 20. Hybridoma culture supernatants were added to wells, and incubated at room temperature for 1 hour. After that, the plate was washed with TBS/0.05% Tween 20. Subsequently, a peroxidase-conjugated mouse anti-IgG antibody diluted with 1% skimmed milk/phosphate buffered saline was added to the wells, followed by incubation at room temperature for 1 hour. After the incubation, the plate was washed with TBS/0.05% Tween 20. A substrate solution (0.05% o-phenylenediamine/citrate buffer (pH 5)/0.03% $H_2O_2$) was added to the wells, and a chromogenic reaction was performed. Ten to fifteen minutes after the addition of the substrate solution, the reaction was stopped by adding 2 N sulfuric acid, and the absorbance at 490 nm was measured with a spectrophotometer. The obtained results are shown in Columns D of Tables 2 and 3.

<Purification of Monoclonal Antibodies>

According to a known method, the culture supernatants of the hybridomas were each filtered through a 0.22-μm filter to remove insoluble matters from the culture supernatant. Subsequently, in a usual manner, the culture supernatant was passed through a column packed with ProteinG-sepharose4B (manufactured by GE Helthecare), so that the antibody components were adsorbed, and then non-specifically adsorbed components were removed by washing the column. Then, the adsorbed IgG was liberated under an acidic condition, and the liberated IgG (a monoclonal antibody) was collected to obtain a purified antibody. In addition, the obtained purified antibody was dialyzed against 100 volumes of PBS to perform buffer exchange.

Note that the isotypes of the 35 anti-NS3 monoclonal antibodies shown in Tables 2 to 5 were identified by using an isotype identification kit (manufactured by Bethyl Laboratories) according the attached protocol.

Example 9

Reporter Assay Using Anti-NS3 Monoclonal Antibodies

The hybridomas positive for the recombinant NS3 were studied in terms of inhibition of the binding between NS3 protease and type I TGF-β receptor (TGF-β-like activity of NS3 protease) achieved by the anti-NS3 monoclonal antibodies produced by the hybridomas. Specifically, first, reporter cells (×9CAGA/CCL64 cells) which were designed to increase luciferase gene expression with increase in signal from type II TGF β receptor were seeded confluently in a 96-well microplate, and cultured overnight under conditions of 37° C. and 5% $CO_2$. After the culture supernatant was removed, the cells were washed with PBS, and the medium was exchanged with a serum-free medium to which the recombinant NS3 was added at a final concentration of 100 μg/mL. Here, to the serum-free medium to which the recombinant NS3 was added, a hybridoma culture supernatant (serum-free) containing an anti-NS3 monoclonal antibody at a known concentration was added at a final concentration of 1 µg/mL or 0.1 µg/mL. In addition, a serum-free medium to which the recombinant NS3 was added but to which no anti-NS3 monoclonal antibody was added was also prepared. Then, the thus prepared cells were cultured overnight at 37° C. in 5% $CO_2$, followed by removal of the culture supernatant and washing with PBS. Subsequently, 30 µL of Passive Lysis buffer (manufactured by Promega) was added to the washed cells, and the cells were lyzed by vigorous stirring at room temperature for 15 minutes. Luciferase Assay substrate (manufactured by Promega) prepared according to a standard protocol was dispensed in a luciferase assay 96-well microplate at 100 µL per well. Moreover, 15 µL of the cell lysate was added to these wells. Then, the microplate to which the cell lysate was added was immediately measured for luciferin fluorescence signal with a fluorescent plate reader. In addition, the degree (binding inhibition %) of the inhibition of the binding between NS3 protease and type I TGF-β receptor achieved by each anti-NS3 monoclonal antibody was calculated by converting the obtained measured value, while the value measured for the serum-free medium to which only the recombinant NS3 was added (the medium to which no anti-NS3 monoclonal antibody was added) was regarded as 100. The obtained results are shown in Column A of Tables 2 and 3. Note that the 35 clones shown in Table 2 to 5 are anti-NS3 monoclonal antibodies prepared in this study and are clones which exhibited an activity (binding inhibition) in this reporter assay or a reactivity (an IP of 10% or higher) with the antigen in the immunoprecipitation-ELISA method.

Example 10

Inhibition of Collagen Production Stimulating Activity of NS3 Protease by Antibodies to Binding Sites Between NS3 Protease and TGF-β Receptor Whether or not the five monoclonal antibodies (anti-NS3 monoclonal antibodies) (the clones shown in Tables 2 to 5: e1211, e0458, s0647, P3-g0948, and P3-g1390) to the binding sites between NS3 protease and TGF-β receptor inhibit the collagen production Stimulating Activity of the NS3 protease was investigated by using human normal hepatocyte-derived cell line Hc cells. The Hc cells were suspended at $4 \times 10^5$ cells/ml in a Dulbecco's modified Eagle's medium (DMEM, manufactured by Invitrogen) to which a 10% fetal bovine serum (manufactured by EQUITECH-BIO) and a 1% antiseptic (a penicillin-streptomycin-glutamine solution, manufactured by Invitrogen) were added. The suspended Hc cells was seeded at 500 µl/well in a 24-well cell culture plate (manufactured by TPP), and cultured overnight at 37° C. in the presence of 5% $CO_2$. Then, the culture supernatant was removed from the plate by suction, and the cells were washed with a calcium-magnesium containing phosphate buffer. Then, DMEM (hereinafter, also referred to as "treatment medium") which contained 0.1% bovine serum albumin (manufactured by EQUITECH-BIO) and the 1% antiseptic and to which one of the anti-NS3 monoclonal antibodies was added was added at 250 µl/well. Here, the anti-NS3 monoclonal antibody clone No. e1211 was added at final concentrations of 0.02, 0.2, 2, and 20 µg/ml, and the other clones were added at a final concentration of 20 µg/ml. Then, culturing was performed at 37° C. in the presence of 5% $CO_2$ for 1 hour. After that a treatment medium to which the recombinant NS3 was added at 100 µg/ml was further added at 250 µl/well. With the final concentrations of the e1211 antibody being 0.01, 0.1, 1, and 10 µg/ml, with the final concentrations of the other clones being 10 µg/ml, and with the final concentration of the recombinant NS3 being 50 µg/ml, culturing was performed at 37° C. in the presence of 5% $CO_2$ for additional 20 hours. In addition, cells (untreated cells) cultured in a treatment medium containing neither the anti-NS3 monoclonal antibodies nor the purified recombinant NS3 protease were prepared as a negative control. Moreover, cells cultured in a treatment medium which contained no anti-NS3 monoclonal antibodies but to which the purified recombinant NS3 protease was added at a final concentration of 50 µg/ml were prepared as a positive control.

Figure 15:
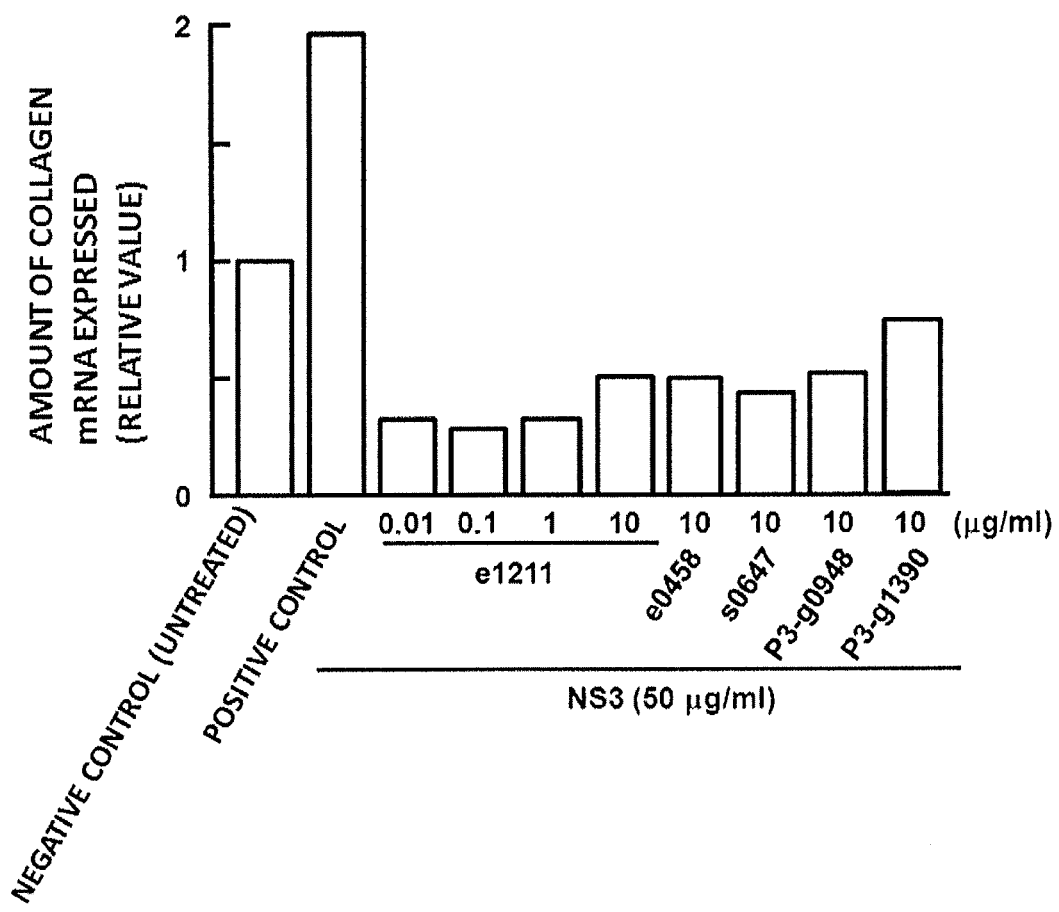
FIG. 15 is a graph showing that anti-NS3 monoclonal antibodies (e1211, e0458, s0647, P3-g0899, and P3-g1390) inhibit collagen production promoted by NS3 protease.

After that, RNAs were extracted from these cells by using TRIzol reagent (manufactured by Invitrogen), and the concentration thereof was determined by measuring the absorbance at 260 nm by using a spectrophotometer (Nano Drop). Subsequently, a RT reaction was carried out by using the RNAs as templates and by using primeScript™ RT reagent Kit (manufactured by TAKARA) according to the package insert. Moreover, a reaction liquid was prepared by using SYBR® Premix Ex Taq™ II (manufactured by TAKARA) according to the package insert, and a PCR reaction was carried out by using primers (manufactured by Invitrogen) for collagen (I) α1 and GAPDH which was an internal standard. The amount of expression of Collagen(I)α1 mRNA was corrected by the amount of expression of GAPDH, and compared with that of the untreated cells (negative control). FIG. 15 shows the obtained results.

As shown in FIG. 15, the NS3 protease increased the amount of collagen expressed in Hc cells by approximately twice (see the negative control and the positive control), and it was shown that such a collagen production stimulating activity of the NS3 protease was inhibited by the anti-NS3 monoclonal antibodies. Among the five anti-NS3 monoclonal antibodies investigated, e1211 exhibited the inhibition activity from the lowest concentration, in particular.

INDUSTRIAL APPLICABILITY

As described above, the present invention makes it possible to provide a compound capable of inhibiting activation of TGF-β receptors due to HCV, and a screening method for the compound, and, in turn, provide a composition for preventing or treating a disease caused by hepatitis C virus.

Moreover, the compound of the present invention and the pharmaceutical composition comprising the compound as an active ingredient have an effect based on an action mechanism of inhibiting binding between NS3 protease and type I TGF-β receptor, and are hence different from agents for treating a disease caused by hepatitis C virus, such as PEG interferon, ribavirin, NS3 protease activity inhibitors, and the like, which are currently used or under development, in the context of action in the pathogenic mechanism of fibrosis of the liver or the like. Hence, the use of the pharmaceutical composition of the present invention in combination with these therapeutic agents which are currently used or under development makes it possible to stop the progression of the pathological condition caused by hepatitis C virus, eliminate the virus, and completely cure a liver disease caused by hepatitis C virus, with reduced concentrations of the drugs used.

SEQUENCE LISTING FREE TEXT

SEQ ID NO: 7

<223> sequence of recombinant protein

The invention claimed is:

1. A method for inhibiting activation of TGF-β receptors due to NS3 protease, the method comprising:
contacting the NS3 protease or the type 1 TGF-β receptors, respectively, with an antibody or antigen binding fragment thereof that binds to the binding site of the NS3 protease, which site binds to type 1 TGF-β receptor or with an antibody or antigen binding fragment thereof that binds to the binding site of type 1 TGF-β receptor, which site binds to the NS3 protease; thereby inhibiting binding between the NS3 protease and type I TGF-β receptor.

2. The method of claim 1, wherein the antibody or antigen binding fragment thereof specifically binds to the amino acid sequence of any one of SEQ ID NOS: 1 to 6.

3. The method of claim 1, wherein the antibody or antigen binding fragment thereof specifically binds to the amino acid sequence of any one of SEQ ID NOS: 1 to 3.

* * * * *

```
SEQUENCE LISTING

<160> NUMBER OF SEQ ID NOS: 14

<210> SEQ ID NO 1
<211> LENGTH: 21
<212> TYPE: PRT
<213> ORGANISM: Hepatitis C virus

<400> SEQUENCE: 1

Thr Gly Arg Asp Lys Asn Gln Val Glu Gly Glu Val Gln Val Val Ser
1               5                   10                  15

Thr Ala Thr Gln Ser
            20

<210> SEQ ID NO 2
<211> LENGTH: 21
<212> TYPE: PRT
<213> ORGANISM: Hepatitis C virus

<400> SEQUENCE: 2

Thr Asn Val Asp Gln Asp Leu Val Gly Trp Pro Ala Pro Pro Gly Ala
1               5                   10                  15

Arg Ser Leu Thr Pro
            20

<210> SEQ ID NO 3
<211> LENGTH: 21
<212> TYPE: PRT
<213> ORGANISM: Hepatitis C virus

<400> SEQUENCE: 3

Arg Gly Asp Asn Arg Gly Ser Leu Leu Ser Pro Arg Pro Val Ser Tyr
1               5                   10                  15

Leu Lys Gly Ser Ser
            20

<210> SEQ ID NO 4
<211> LENGTH: 16
<212> TYPE: PRT
<213> ORGANISM: Homo sapiens

<400> SEQUENCE: 4

Phe Val Ser Val Thr Glu Thr Thr Asp Lys Val Ile His Asn Ser Met
1               5                   10                  15

<210> SEQ ID NO 5
<211> LENGTH: 14
<212> TYPE: PRT
<213> ORGANISM: Homo sapiens

<400> SEQUENCE: 5

Ile Ala Glu Ile Asp Leu Ile Pro Arg Asp Arg Pro Phe Val
1               5                   10

<210> SEQ ID NO 6
<211> LENGTH: 14
<212> TYPE: PRT
<213> ORGANISM: Homo sapiens
```

<400> SEQUENCE: 6

Cys Ala Pro Ser Ser Lys Thr Gly Ser Val Thr Thr Thr Tyr
1               5                   10

<210> SEQ ID NO 7
<211> LENGTH: 195
<212> TYPE: PRT
<213> ORGANISM: Artificial Sequence
<220> FEATURE:
<223> OTHER INFORMATION: Synthetic polypeptide

<400> SEQUENCE: 7

Gly Ser Val Val Ile Val Gly Arg Ile Ile Leu Ser Gly Ser Gly Ser
1               5                   10                  15

Pro Ile Thr Ala Tyr Ser Gln Gln Thr Arg Gly Leu Leu Gly Cys Ile
                20                  25                  30

Ile Thr Ser Leu Thr Gly Arg Asp Lys Asn Gln Val Glu Gly Glu Val
            35                  40                  45

Gln Val Val Ser Thr Ala Thr Gln Ser Phe Leu Ala Thr Cys Val Asn
        50                  55                  60

Gly Val Cys Trp Thr Val Tyr His Gly Ala Gly Ser Lys Thr Leu Ala
65                  70                  75                  80

Gly Pro Lys Gly Pro Ile Ala Gln Met Tyr Thr Asn Val Asp Gln Asp
                85                  90                  95

Leu Val Gly Trp Pro Ala Pro Gly Ala Arg Ser Leu Thr Pro Cys
                100                 105                 110

Thr Cys Gly Ser Ser Asp Leu Tyr Leu Val Thr Arg His Ala Asp Val
            115                 120                 125

Ile Pro Val Arg Arg Arg Gly Asp Asn Arg Gly Ser Leu Leu Ser Pro
130                 135                 140

Arg Pro Val Ser Tyr Leu Lys Gly Ser Ser Gly Gly Pro Leu Leu Cys
145                 150                 155                 160

Pro Ser Gly His Ala Val Gly Val Phe Arg Ala Ala Val Cys Thr Arg
                165                 170                 175

Gly Val Ala Lys Ala Val Asp Phe Val Pro Val Glu Ser Met Glu Thr
            180                 185                 190

Thr Met Arg
        195

<210> SEQ ID NO 8
<211> LENGTH: 181
<212> TYPE: PRT
<213> ORGANISM: Hepatitis C virus

<400> SEQUENCE: 8

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
                20                  25                  30

Val Gln Val Val Ser Thr Ala Thr Gln Ser Phe Leu Ala Thr Cys Val
            35                  40                  45

Asn Gly Val Cys Trp Thr Val Tyr His Gly Ala Gly Ser Lys Thr Leu
        50                  55                  60

Ala Gly Pro Lys Gly Pro Ile Ala Gln Met Tyr Thr Asn Val Asp Gln
65                  70                  75                  80

Asp Leu Val Gly Trp Pro Ala Pro Pro Gly Ala Arg Ser Leu Thr Pro

```
                     85                  90                  95
Cys Thr Cys Gly Ser Ser Asp Leu Tyr Leu Val Thr Arg His Ala Asp
            100                 105                 110

Val Ile Pro Val Arg Arg Gly Asp Asn Arg Gly Ser Leu Leu Ser
        115                 120                 125

Pro Arg Pro Val Ser Tyr Leu Lys Gly Ser Ser Gly Pro Leu Leu
    130                 135                 140

Cys Pro Ser Gly His Ala Val Gly Val Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg Ser
            180

<210> SEQ ID NO 9
<211> LENGTH: 79
<212> TYPE: PRT
<213> ORGANISM: Homo sapiens

<400> SEQUENCE: 9

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 10
<211> LENGTH: 22
<212> TYPE: PRT
<213> ORGANISM: Artificial Sequence
<220> FEATURE:
<223> OTHER INFORMATION: Synthetic peptide

<400> SEQUENCE: 10

Cys Thr Gly Arg Asp Lys Asn Gln Val Glu Gly Glu Val Gln Val Val
1               5                   10                  15

Ser Thr Ala Thr Gln Ser
            20

<210> SEQ ID NO 11
<211> LENGTH: 22
<212> TYPE: PRT
<213> ORGANISM: Artificial Sequence
<220> FEATURE:
<223> OTHER INFORMATION: Synthetic peptide

<400> SEQUENCE: 11

Cys Thr Asn Val Asp Gln Asp Leu Val Gly Trp Pro Ala Pro Pro Gly
1               5                   10                  15

Ala Arg Ser Leu Thr Pro
            20

<210> SEQ ID NO 12
<211> LENGTH: 22
<212> TYPE: PRT
```

```
<213> ORGANISM: Artificial Sequence
<220> FEATURE:
<223> OTHER INFORMATION: Synthetic peptide

<400> SEQUENCE: 12

Cys Arg Gly Asp Asn Arg Gly Ser Leu Leu Ser Pro Arg Pro Val Ser
1               5                   10                  15

Tyr Leu Lys Gly Ser Ser
            20

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Polyethylene spacer of 6000 Da between
      residues 1 and 2

<400> SEQUENCE: 13

Cys Phe Val Ser Val Thr Glu Thr Thr Asp Lys Val Ile His Asn Ser
1               5                   10                  15

Met

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Polyethylene glycol spacer of 6000 Da
      between residues 1 and 2

<400> SEQUENCE: 14

Cys Ile Ala Glu Ile Asp Leu Ile Pro Arg Asp Arg Pro Phe Val
1               5                   10                  15
```